(12) United States Patent
Imura et al.

(10) Patent No.: US 7,452,970 B2
(45) Date of Patent: Nov. 18, 2008

(54) HUMAN ENDOTHELIN RECEPTOR

(75) Inventors: Hiroo Imura, Kyoto (JP); Kazuwa Nakao, Kyoto (JP); Shigetada Nakanishi, Kyoto (JP)

(73) Assignee: Shionogi Seiyaku Kabushiki Kaisha, Osaka-shi (JP)

( * ) Notice: Subject to any disclaimer, the term of this patent is extended or adjusted under 35 U.S.C. 154(b) by 817 days.

(21) Appl. No.: 10/934,973

(22) Filed: Sep. 3, 2004

(65) Prior Publication Data

US 2008/0119638 A1 May 22, 2008

Related U.S. Application Data

(60) Continuation of application No. 09/931,157, filed on Aug. 16, 2001, now Pat. No. 6,821,743, which is a division of application No. 08/121,446, filed on Sep. 14, 1993, now Pat. No. 6,313,276, which is a continuation of application No. 07/911,684, filed on Jul. 10, 1992, now abandoned.

(30) Foreign Application Priority Data

Jul. 12, 1991 (JP) ................................. 3-172828

(51) Int. Cl.
C07K 14/435 (2006.01)
C07K 14/705 (2006.01)
C12P 21/02 (2006.01)
A61K 38/17 (2006.01)

(52) U.S. Cl. .............................. 530/350; 514/2; 514/12; 536/23.5; 435/69.1

(58) Field of Classification Search ........................ None
See application file for complete search history.

(56) References Cited

U.S. PATENT DOCUMENTS 5,464,853 A 11/1995 Chan et al.
5,837,241 A 11/1998 Ferrara et al.
6,432,994 B1 8/2002 Wu et al.
6,545,048 B1 4/2003 Patterson et al.
6,821,743 B2 11/2004 Imura et al.

FOREIGN PATENT DOCUMENTS

EP 0 480 381 4/1992

OTHER PUBLICATIONS

Adachi et al. (1991). "Cloning and Characterization of the cDNA Encoding Human A-type Endothelial Receptor," *Biophys. Res. Comm.* 180(3):1265-1272.
Arai et al. (1990). "Cloning and Expression of a cDNA Encoding an Endothelin Receptor," *Nature* 348(6303):730-773.
Cyr et al. (1991). "Cloning and Chromosomal Localization of a Human endothelial ETA Receptor," *Biochem. Biophys. Res. Comm.* 181(1):184-190.
Hosoda et al. (1991). "Cloning and Expressions of Human Endothelial-1 Receptor cDNA," *FEBS Letters* 287(I, 2):23-26.
Inoue et al. (1989). "The Human Endothelin Family: Three Structurally and Pharmcologically Distinct Isopeptides Predicted by Three Separate Genes," *Proc. Natl. Acad. Sci. USA* 86(8):2863-2867.
Kloog et al. (1989). "Three Apparent Receptor Subtypes for the Endothelin /Sarafotoxin Family," *FEBS Letters* 253(1-2):199-202.
Lin et al. (1992). "Cloning and Functional Expression of a Vascular Smooth Muscle Endothelin 1 Receptor," *Chem. Abstracts* 116(9):165.
Lin, H. Y. et al. (1991). "Cloning and Functional Expression of a Vascular Smooth Muscle Endothelin 1 Receptor," *Proc. Natl. Acad. Sci. USA* 88(8):3185-3189.
MacCumber et al. (1990). "Endothelin in Brain: Receptors, Mitogenesis, and Biosynthesis in Glial Cells," *Proc. Natl. Acad. Sci USA* 87(6):2359-2363.
Maggi et al. (1991). "Immunolocalization, Binding, and Biological Activity of Endothelin in Rabbit Uterus: Effect of Ovarian Steroids," *American Journal of Physiology* 260(2, Pt 1): E292-E305.
Martin et al. (1990). "Heterogenicity of Cell Surface Endothelin Receptors," *Natl. J. Biol. Chem.* 265(23):14044-14049.
Masu et al. (1987). "cDNA Cloning of Bovine Substance-K Receptor Through Oocyte Expression System," *Nature* 329(6142):836-838.
Masuda et al. (1989). "Two Different Forms of Endothelin Receptors in Rat Lung," *FEBS Letters* 257(2):208-210.
Nakamuta et al. (1991). "Cloning and Sequence Analysis of a cDNA Encoding Human Non-Selective Type of Endothelin Receptor," *Biochem. Biophys. Res. Comm.* 177(1):34-36.
Nakamuta et al. (1992). "Cloning and Sequence Analysis of a cDNA Encoding Human Endothelin Receptor," *Biochem. Biophys. Res. Comm.* 178(1)248-255.
Ogawa et al. (1991). "Molecular Cloning of a Non-Isopeptide-Selective Human Endothelin Receptor," *Biochem. Biophys. Res. Comm* 178(1):248-255.
Ogawa et al. (1992). "Molecular Cloning of a Non-Isopeptide Selective Human Endothelin Receptor," *Chem. Abstracts* 116(13):230.
Sakamoto et al. (1991). "Cloning and Functional Expression of Human cDNA for the $ET_B$ Endothelin Receptor," *Biochem. Biophys. Res. Comm.* 178(2):656-663.
Sakamoto et al. (1992). "Cloning of a cDNA Encoding a Non-Isopeptide-Selective Subtype of the Endothelin Receptor," *Nature* 348(6303):732-735.

(Continued)

*Primary Examiner*—Christine J Saoud
*Assistant Examiner*—Jon M Lockard
(74) *Attorney, Agent, or Firm*—Morrison & Foerster LLP

(57) ABSTRACT

DNA encoding an endothelin receptor shown in SEQ ID NO: 1 or 2 in the Sequence Listing is isolated from cDNA which is prepared from poly(A)+ RNA derived from a human placenta. In addition, an expression vector containing the DNA and a transformant containing the expression vector are obtained. An endothelin receptor is obtained by culturing this transformant. A receptor shown in SEQ ID NO: 1 is an $ET_A$-receptor which has a high affinity for endothelins 1 and 2, especially for the endothelin 1. A receptor shown in SEQ ID NO: 2 is an $ET_B$-receptor which has an affinity for endothelins 1, 2 and 3 with no selectivity.

4 Claims, 16 Drawing Sheets

OTHER PUBLICATIONS

Sakurai et al. (1990). "Cloning of cDNA Encoding a Non-Isopeptide -Selective Subtype of the Endothelin Receptor," *Nature* 348(6303):732-735.

Shimada et al. (1991). "Endothelin Receptor: a Profoundly Desensitizing Receptor Expressed in Xenopus oocytes," *Eur. J. Pharmacol* 193(1):123-125.

Simonson et al. (1990). "Cellular Signaling by Peptides of the Endothelin Gene Family," *FASEB Journal* 4(12):2989-3000.

Wada et al. (1990). "Purification of an Endothelin Receptor from Human Placenta," *Biochem. Biophys. Res. Comm.* 167(1):251-257.

Watanabe et al. (1989). "Two Distinct Types of Endothelin Receptors are Present on Chick Cardiac Membranes," *Biochem. Biophsys. Res. Comm.* 161(3):1252-1259.

Wenzel et al. (May 1994). "Endothelin Receptor Antagonists Inhibit Endothelin in Human Skin Microcirculation," *Hypertension* 23(5):581-586.

Yanagisawa et al. (1988). "A Novel Potent Vasoconstrictor Peptide Produced by Vascular Endothelial Cells," *Nature* 332:411-415.

Yanagisawa et al. (1989). "Molecular Biology and Biochemistry of the Endothelins," *Trends Pharmacol. Sci* 10(9):374-378.

Fig. 1A  SEQ ID NO: 1

```
GAATTCGCGG CCGCCTCTTG CGGTCCCAGA GTGGAGTGGA AGGTCTGGAG CTTTGGGAGG      60
AGACGGGGAG GACAGACTGG AGGCGTGTTC CTCCCGGATT TTCTTTTTCG TGCCAGCCCT     120
CGCGCGCGCG TACAGTCATC CCGCTGGTCT GACGATTGTG GAGAGGCGGT GGAGAGGCTT     180
CATCCATCCC ACCCGGTCGT CGCCGGGGAT TGGGGTCCCA GCGACACCTC CCCGGGAGAA     240
GCAGTGCCCA GGAAGTTTTC TGAAGCCGGG GAAGCTGTGC AGCCGAAGCC GCCGCCGCGC     300
CGGAGCCCGG GACACCGGCC ACCCTCCGCG CCACCCACCC TCGCTTTCTC CGGCTTCCTC     360
TGCCCAGGC  GCCGCGCGGA CCCGGCAGCT GTCTGCCGCAC GCCGAGCTCC ACGGTGAAAA    420
AAAAAGTGAA GGTGTAAAAG CAGCACAAGT GCAATAAGAG ATATTTCCTC AAATTTGCCT     480
```

```
CAAG ATG GAA ACC CTT TGC CTC AGG GCA TCC TTT TGG CTG GCA CTG GTT     529
     Met Glu Thr Leu Cys Leu Arg Ala Ser Phe Trp Leu Ala Leu Val
     -20              -15                 -10                          577
GGA TGT GTA ATC AGT GAT AAT CCT GAG AGA TAC AGC ACA AAT CTA AGC
Gly Cys Val Ile Ser Asp Asn Pro Glu Arg Tyr Ser Thr Asn Leu Ser
 -5       -1  1               5                    10
AAT CAT GTG GAT GAT TTC ACC ACT TTT CGT GGC ACA GAG CTC AGC TTC     625
Asn His Val Asp Asp Phe Thr Thr Phe Arg Gly Thr Glu Leu Ser Phe
              15                  20                  25
CTG GTT ACC ACT CAT CAA CCC ACT AAT TTG GTC CTA CCC AGC AAT GGC     673
Leu Val Thr Thr His Gln Pro Thr Asn Leu Val Leu Pro Ser Asn Gly
              30                  35                  40
TCA ATG CAC AAC TAT TGC CCA CAG CAG ACT AAA ATT ACT TCA GCT TTC     721
Ser Met His Asn Tyr Cys Pro Gln Gln Thr Lys Ile Thr Ser Ala Phe
              45                  50                  55
AAA TAC ATT AAC ACT GTG ATA TCT TGT ACT ATT TTC ATC GTG GGA ATG     769
Lys Tyr Ile Asn Thr Val Ile Ser Cys Thr Ile Phe Ile Val Gly Met
              60                  65                  70        75
```

Fig. 1B

| | |
|---|---:|
| GTG GGG AAT GCA ACT CTG CTC AGG ATC ATT TAC CAG AAC AAA TGT ATG<br>Val Gly Asn Ala Thr Leu Leu Arg Ile Ile Tyr Gln Asn Lys Cys Met<br>                80                    85                  90 | 817 |
| AGG AAT GGC CCC AAC GCG CTG ATA GCC AGT CTT GCC CTT GGA GAC CTT<br>Arg Asn Gly Pro Asn Ala Leu Ile Ala Ser Leu Ala Leu Gly Asp Leu<br>                95                  100              105 | 865 |
| ATC TAT GTG GTC ATT GAT CTC CCT ATC AAT GTA TTT AAG CTG CTG GCT<br>Ile Tyr Val Val Ile Asp Leu Pro Ile Asn Val Phe Lys Leu Leu Ala<br>            110                  115              120 | 913 |
| GGG CGC TGG CCT TTT GAT CAC AAT GAC TTT GGC GTA TTT CTT TGC AAG<br>Gly Arg Trp Pro Phe Asp His Asn Asp Phe Gly Val Phe Leu Cys Lys<br>            125                  130              135 | 961 |
| CTG TTC CCC TTT TTG CAG AAG TCC TCG GTG GGG ATC ACC GTC CTC AAC<br>Leu Phe Pro Phe Leu Gln Lys Ser Ser Val Gly Ile Thr Val Leu Asn<br>140                  145                  150              155 | 1009 |
| CTC TGC GCT CTT AGT GTT GAC AGG TAC AGA GCA GTT GCC TCC TGG AGT<br>Leu Cys Ala Leu Ser Val Asp Arg Tyr Arg Ala Val Ala Ser Trp Ser<br>            160                  165              170 | 1057 |
| CGT GTT CAG GGA ATT GGG ATT CCT TTG GTA ACT GCC ATT GAA ATT GTC<br>Arg Val Gln Gly Ile Gly Ile Pro Leu Val Thr Ala Ile Glu Ile Val<br>            175                  180              185 | 1105 |
| TCC ATC TGG ATC CTG TCC TTT ATC CTG GCC ATT CCT GAA GCG ATT GGC<br>Ser Ile Trp Ile Leu Ser Phe Ile Leu Ala Ile Pro Glu Ala Ile Gly<br>            190                  195              200 | 1153 |
| TTC GTC ATG GTA CCC TTT GAA TAT AGG GGT GAA CAG CAT AAA ACC TGT<br>Phe Val Met Val Pro Phe Glu Tyr Arg Gly Glu Gln His Lys Thr Cys<br>            205                  210              215 | 1201 |

Fig. 1C

| | |
|---|---|
| ATG CTC AAT GCC ACA TCA AAA TTC ATG GAG TTC TAC CAA GAT GTA AAG<br>Met Leu Asn Ala Thr Ser Lys Phe Met Glu Phe Tyr Gln Asp Val Lys<br>220               225               230               235 | 1249 |
| GAC TGG TGG CTC TTC GGG TTC TAT TTC TGT ATG CCC TTG GTG TGC ACT<br>Asp Trp Trp Leu Phe Gly Phe Tyr Phe Cys Met Pro Leu Val Cys Thr<br>               240               245               250 | 1297 |
| GCG ATC TTC TAC ACC CTC ATG ACT TGT GAG ATG TTG AAC AGA AGG AAT<br>Ala Ile Phe Tyr Thr Leu Met Thr Cys Glu Met Leu Asn Arg Arg Asn<br>               225               260               265 | 1345 |
| GGC AGC TTG AGA ATT GCC CTC AGT GAA CAT CTT AAG CAG CGT CGA GAA<br>Gly Ser Leu Arg Ile Ala Leu Ser Glu His Leu Lys Gln Arg Arg Glu<br>               270               275               280 | 1393 |
| GTG GCA AAA ACA GTT TTC TGC TTG GTT GTA ATT TTT GCT CTT TGC TGG<br>Val Ala Lys Thr Val Phe Cys Leu Val Val Ile Phe Ala Leu Cys Trp<br>285               290               295 | 1441 |
| TTC CCT CTT CAC TTA AGC CGT ATA TTG AAG AAA ACT GTG TAT AAC GAA<br>Phe Pro Leu His Leu Ser Arg Ile Leu Lys Lys Thr Val Tyr Asp Glu<br>300               305               310               315 | 1489 |
| ATG GAC AAG AAC CGA TGT GAA TTA CTT AGT TTC TTA CTG CTC ATG GAT<br>Met Asp Lys Asn Arg Cys Glu Leu Leu Ser Phe Leu Leu Leu Met Asp<br>               320               325               330 | 1537 |
| TAC ATC GGT ATT AAC TTG GCA ACC ATG AAT TCA TGT ATA AAC CCC ATA<br>Tyr Ile Gyr Ile Asn Leu Ala Thr Met Asn Ser Cys Lle Asn Pro Ile<br>               335               340               345 | 1585 |
| GCT CTG TAT TTT GTG AGC AAG AAA TTT AAA AAT TGT TTC CAG TCA TGC<br>Ala Leu Tyr Phe Val Ser Lys Lys Phe Lys Asn Cys Phe Gln Ser Cys<br>               350               355               360 | 1633 |

Fig. 1D

| | |
|---|---|
| CTC TGC TGC TGC TGT TAC CAG TCC AAA AGT CTG ATG ACC TCG GTC CCC<br>Leu Cys Cys Cys Cys Tyr Gln Ser Lys Ser Leu Met Thr Ser Val Pro<br>365                    370                 375 | 1681 |
| ATG AAC GGA ACA AGC ATC CAG TGG AAG AAC CAC GAT CAA AAC AAC CAC<br>Met Asn Gly Thr Ser Ile Gln Trp Lys Asn His Asp Gln Asn Asn His<br>380                    385                 390                  395 | 1729 |
| AAC ACA GAC CGG AGC AGC CAT AAG GAC AGC ATG AAC TGACCACCCT<br>Asn Thr Asp Arg Ser Ser His Lys Asp Ser Met Asn<br>                 400                  405 | 1775 |
| TAGAAGCACT CCTCGGTACT CCCATAATCC TCTCGGAGAA AAAAATCACA AGGCAACTGT | 1835 |
| GACTCCGGGA ATCTCTTCTC TGATCCTTCT TCCTTAATTC ACTCCCACAC CCAAGAAGAA | 1895 |
| ATGCTTTCCA AAACCGCAAG GTAGACTGGT TTATCCACCC ACAACATCTA CGAATCGTAC | 1955 |
| TTCTTTAATT GATCTAATTT ACATATTCTG CGTGTTGTAT TCAGCACTAA AAAATGGTGG | 2015 |
| GAGCTGGGGG AGAATGAAGA CTGTTAAATG AAACCAGAAG GATATTTACT ACTTTTGCAT | 2075 |
| GAAAATAGAG CTTTCAAGTA CATGGCTAGC TTTTATGGCA GTTCTGGTGA ATGTTCAATG | 2135 |
| GGAACTGGTC ACCATGAAAC TTTAGAGATT AACGACAAGA TTTTCTACTT TTTTTAAGTG | 2195 |
| ATTTTTTGTC CTTCAGCCAA ACACAATATG GGCTCAGGTC ACTTTTATTT GAAATGTCAT | 2255 |
| TTGGTGCCAG TATTTTTTAA CTGCATAATA GCCTAACATG ATTATTTGAA CTTATTTACA | 2315 |
| CATAGTTTGA AAAAAAAAAG ACAAAAATAG TATTCAGGTG AGCAATTAGA TTAGTATTTT | 2375 |
| CCACGTCACT ATTTATTTTT TTAAAACACA AATTCTAAAG CTACAACAAA TACTACAGGC | 2435 |
| CCTTAAAGCA CAGTCTGATG ACACATTTGG CAGTTTAATA GATGTTACTC AAAGAATTTT | 2495 |
| TTAAGAACTG TATTTTATTT TTTAAATGGT GTTTTATTAC AAGGGACCTT GAACATGTTT | 2555 |
| TGTATGTTAA ATTCAAAAGT AATGCTTCAA TCAGATAGTT CTTTTTCACA AGTTCAATAC | 2615 |
| TGTTTTTCAT GTAAATTTTG TATGAAAAAT CAATGTCAAG TACCAAAATG TTAATGTATG | 2675 |
| TGTCATTTAA CTCTGCCTGA GACTTTCAGT GCACTGTATA TAGAAGTCTA AAACACACCT | 2735 |
| AAGAGAAAAA GATCGAATTT TTCAGATGAT TCGGAAATTT TCATTCAGGT ATTTGTAATA | 2795 |

Fig. 1E

```
GTGACATATA TATGTATATA CATATCACCT CCTATTCTCT TAATTTTTGT TAAAATGTTA    2855
ACTGGCAGTA AGTCTTTTTT GATCATTCCC TTTTCCATAT AGGAAACATA ATTTTGAAGT    2915
GGCCAGATGA GTTTATCATG TCAGTGAAAA ATAATTACCC ACAAATGCCA CCAGTAACTT    2975
AACGATTCTT CACTTCTTGG GGTTTTCAGT ATGAACCTAA CTCCCCACCC CAACATCTCC    3035
CTCCCACATT GTCACCATTT CAAAGGGCCC ACAGTGACTT TGCTGGGCA TTTTCCCAGA     3095
TGTTTACAGA CTGTGAGTAC AGCAGAAAAT CTTTTACTAC TGTGTGTGTG TATATATATA    3155
AACAATTGTA AATTTCTTTT AGCCCATTTT TCTAGACTGT CTCTGTGGAA TATATTTGTG    3215
TGTGTGATAT ATGCATGTGT GTGATGGTAT GTATGGATTT AATCTAATCT AATAATTGTG    3275
CCCCGCAGTT GTGCCAAAGT GCATAGTCTG AGCTAAAATC TAGGTGATTG TTCATCATGA    3335
CACCCTGCCT CAGTCCATTT TAACCTGTAG CAACCTTCTG CATTCATAAA TCTTGTAATC    3395
ATGTTACCAT TACAAATGGG ATATAAGAGG CAGCGTGAAA GCAGATGAGC TGTGGACTAG    3455
CAATATAGGG TTTTGTTTGG TTGGTTGGTT TGATAAAGCA GTATTTGGGG TCATATTGTT    3515
TCCTGTGCTG GAGCAAAAGT CATTACACTT TGAAGTATTA TATTGTTCTT ATCCTCAATT    3575
CAATGTGGTG ATGAAATTGC CAGGTTGTCT GATATTTCTT TCAGACTTCG CCAGACAGAT    3635
TGCTGATAAT AAATTAGGTA AGATAATTTG TTGGGCCATA TTTTAGGACA GGTAAAATAA    3695
CATCAGGTTC CAGTTGCTTG AATTGCAAGG CTAAGAAGTA CTGCCCTTTT GTGTGTTAGC    3755
AGTCAAATCT ATTATTCCAC TGGCGCATCA TATGCAGTGA TATATGCCTA TAATATAAGC    3815
CATAGGTTCA CACCATTTTG TTTAGACAAT TGTCTTTTTT TCAAGATGCT TTGTTTCTTT    3875
CATATGAAAA AAATGCATTT TATAAATTCA GAAAGTCATA GATTTCTGAA GGCGTCAACG    3935
TGCATTTTAT TTATGGACTG GTAAGTAACT GTGGTTTACT AGCAGGAATA TTTCCAATTT    3995
CTACCTTTAC TACATCTTTT CAACAAGTAA CTTTGTAGAA ATGAGCCAGA AGCCAAGGCC    4055
CTGAGTTGGC AGTGGCCCAT AAGTGTAAAA TAAAAGTTTA CAGAAACCTT              4105
```

Fig. 2A   SEQ ID NO: 2

```
GAGACATTCC GGTGGGGGAC TCTGGCCAGC CCGAGCAACG TGGATCCTGA GAGCACTCCC    60
AGGTAGGCAT TTGCCCCGGT GGGACGCCTT GCCAGACCAG TGTGTGGCAG GCCCCCGTGG   120
AGGATCAACA CAGTGGCTGA ACACTGGGAA GGAACTGGTA CTTGGAGTCT GGACATCTGA   180
AACTTGGCTC TGAAACTGCG GAGCGGCCAC CGGACGCCTT CTGGAGCAGG TAGCAGC      237
```

| Codons | AA | Pos |
|---|---|---|
| ATG CAG CCG CCT CCA AGT CTG TGC GGA CGC GCC CTG GTT GCG CTG GTT | Met Gln Pro Pro Pro Ser Leu Cys Gly Arg Ala Leu Val Ala Leu Val | 285 |
|  | 1       5        10       15 |  |
| CTT GCC TGC GGC CTG TCG CGG ATC TGG GGA GAG GAG AGA GGC TTC CCG | Leu Ala Cys Gly Leu Ser Arg Ile Trp Gly Glu Glu Arg Gly Phe Pro | 333 |
|  | 20       25       30 |  |
| CCT GAC AGG GCC ACT CCG CTT TTG CAA ACC GCA GAG ATA ATG ACG CCA | Pro Asp Arg Ala Thr Pro Leu Leu Gln Thr Ala Glu Ile Met Thr Pro | 381 |
|  | 35       40       45 |  |
| CCC ACT AAG ACC TTA TGG CCC AAG GGT TCC AAC GCC AGT CTG GCG CGG | Pro Thr Lys Thr Leu Trp Pro Lys Gly Ser Asn Ala Ser Leu Ala Arg | 429 |
|  | 50       55       60 |  |
| TCG TTG GCA CCT GCG GAG GTG CCT AAA GGA GAC AGG ACG GCA GGA TCT | Ser Leu Ala Pro Ala Glu Val Pro Lys Gly Asp Arg Thr Ala Gly Ser | 477 |
|  | 65       70       75       80 |  |
| CCG CCA CGC ACC ATC TCC CCT CCC CCG TGC CAA GGA CCC ATC GAG ATC | Pro Pro Arg Thr Ile Ser Pro Pro Pro Cys Gln Gly Pro Ile Glu Ile | 525 |
|  | 85       90       95 |  |
| AAG GAG ACT TTC AAA TAC ATC AAC ACG CTT GTG TCC TGC CTT GTG TTC | Lys Glu Thr Phe Lys Tyr Ile Asn Thr Val Val Ser Cys Leu Val Phe | 573 |
|  | 100      105      110 |  |

Fig. 2B

| | |
|---|---|
| GTG CTG GGG ATC ATC GGG AAC TCC ACA CTT CTG AGA ATT ATC TAC AAG | 621 |
| Val Leu Gly Ile Ile Gly Asn Ser Thr Leu Leu Arg Ile Ile Tyr Lrs | |
| 115           120           125 | |
| AAC AAG TGC ATG CGA AAC GGT CCC AAT ATC TTG ATC GCC AGC TTG GCT | 669 |
| Asn Lys Gys Met Arg Asn Gly Pro Asn Ile Leu Ile Ala Ser Leu Ala | |
| 130           135           140 | |
| CTG GGA GAC CTG CTG CAC ATC GTC ATT GAC ATC CCT ATC AAT GTC TAC | 717 |
| Leu Gly Asp Leu Leu His Ile Val Ile Asp Ile Pro Ile Asn Val Tyr | |
| 145           150           155           160 | |
| AAG CTG CTG GCA GAG GAC TGG CCA TTT GGA GCT GAG ATG TGT AAG CTG | 765 |
| Lys Leu Leu Ala Glu Asp Trp Pro Phe Gly Ala Glu Met Cys Lys Leu | |
| 165           170           175 | |
| GTG CCT TTC ATA CAG AAA GCC TCC GTG GGA ATC ACT GTG CTG AGT CTA | 813 |
| Val Pro Phe Ile Gln Lys Ala Ser Val Gly Ile Thr Val Leu Ser Leu | |
| 180           185           190 | |
| TGT GCT CTG AGT ATT GAC AGA TAT CGA GCT GTT GCT TCT TGG AGT AGA | 861 |
| Cys Ala Leu Ser Ile Asp Arg Tyr Arg Ala Val Ala Ser Trp Ser Arg | |
| 195           200           205 | |
| ATT AAA GGA ATT GGG GTT CCA AAA TGG ACA GCA GTA GAA ATT GTT TTG | 909 |
| Ile Lys Gly Ile Gly Val Pro Lys Trp Thr Ala Val Glu Ile Val Leu | |
| 210           215           220 | |
| ATT TGG GTG GTC TCT GTG GTT CTG GCT GTC CCT GAA GCC ATA GGT TTT | 957 |
| Ile Trp Val Val Ser Val Val Leu Ala Val Pro Glu Ala Ile Gly Phe | |
| 225           230           235           240 | |
| GAT ATA ATT ACG ATG GAC TAC AAA GGA AGT TAT CTG CGA ATC TGC TTG | 1005 |
| Asp Ile Ile Thr Met Asp Tyr Lys Gly Ser Tyr Leu Arg Ile Cys Leu | |
| 245           250           255 | |

Fig. 2C

| | |
|---|---|
| CTT CAT CCC GTT CAG AAG ACA GCT TTC ATG CAG TTT TAC AAG ACA GCA<br>Leu His Pro Val Gln Lys Thr Ala Phe Met Gln Phe Tyr Lys Thr Ala<br>260         265         270 | 1053 |
| AAA GAT TGG TGG CTG TTC AGT TTC TAT TTC TGC TTG CCA TTG GCC ATC<br>Lys Asp Typ Trp Leu Phe Ser Phe Tyr Phe Cys Leu Pro Leu Ala Ile<br>275         280         285 | 1101 |
| ACT GCA TTT TTT TAT ACA CTA ATG ACC TGT GAA ATG TTG AGA AAG AAA<br>Thr Ala Phe Phe Tyr Thr Leu Met Thr Cys Glu Met Leu Arg Lys Lys<br>290         295         300 | 1149 |
| AGT GGC ATG CAG ATT GCT TTA AAT GAT CAC CTA AAG CAG AGA CGG GAA<br>Ser Gly Met Gln Ile Ala Leu Asn Asp His Leu Lys Gln Arg Arg Glu<br>305         310         315         320 | 1197 |
| GTG GCC AAA ACC GTC TTT TGC CTG GTC CTT GTC TTT GCC CTC TGC TGG<br>Val Ala Lys Thr Val Phe Cys Leu Val Leu Val Phe Ala Leu Cys Trp<br>325         330         335 | 1245 |
| CTT CCC CTT CAC CTC AGC AGG ATT CTG AAG CTC ACT GTT TAT AAT CAG<br>Leu Pro Leu His Leu Ser Arg Ile Leu Lys Leu Thr Leu Tyr Asp Gln<br>340         345         350 | 1293 |
| AAT GAT CCC AAT AGA TGT GAA CTT TTG AGC TTT CTG TTG GTA TTG GAC<br>Asn Asp Pro Asn Arg Cys Glu Leu Leu Ser Phe Leu Leu Val Leu Asp<br>355         360         365 | 1341 |
| TAT ATT GGT ATG AAC ATG GCT TCA CTG AAT TCC TGC ATT AAC CCA ATT<br>Tyr Ile Gyr Ile Asn Met Ala Ser Leu Asn Ser Cys Ile Asn Pro Ile<br>370         375         380 | 1389 |
| GCT CTG TAT TTC GTG AGC AAA AGA TTC AAA AAC TGC TTT AAG TCA TGC<br>Ala Leu Tyr Leu Val Ser Lys Arg Phe Lys Asn Cys Phe Lys Ser Cys<br>385         390         395         400 | 1437 |

Fig. 2D

```
TTA TGC TGC TGG TGC CAG TCA TTT GAA GAA AAA CAG TCC TTG GAG GAA        1485
Leu Cys Cys Trp Cys Gln Ser Phe Glu Glu Lys Gln Ser Leu Glu Glu
              405             410             415
AAG CAG TCG TGC TTA AAG TTC AAA GCT AAT GAT CAC GGA TAT GAC AAC        1533
Lys Gln Ser Cys Leu Lys Phe Lys Ala Asn Asp His Gly Tyr Asp Asn
              420             425             430
TTC CGT TCC AGT AAT AAA TAC AGC TCA TCT TGAAAGAAGA ACTATTCACT          1583
Phe Arg Ser Ser Asn Lys Tyr Ser Ser Ser
              435             440
GTATTTCATT TTCTTTATAT TGGACGGAAG TCATTAAAAC AAAATGAAAC ATTTGCCAAA      1643
ACAAAACAAA AAACTATGTA TTTGCACAGC ACACTATTAA AATATTAAGT GTAATTATTT      1703
TAACACTCAC AGCTACATAT GACATTTTAT GAGCTGTTTA CGGCATGGAA AGAAAATCAG      1763
AGGGAATTAA GAAAGCCTCG TCGTGAAAGC ACTTAATTTT TTACAGTTAG CACTTCAACA      1823
TAGCTCTTAA CAACTTCCAG GATATTCACA CAACACTTAG GCTTAAAAAT GAGCTCACTC      1883
AGAATTTCTA TTCTTTCTAA AAAGAGATTT ATTTTTAAAT CAATGGGACT CTGATATAAA      1943
GGAAGAATAA GTCACTGTAA AACAGAACTT TTAAATGAAG CTTAAATTAC TCAATTTAAA      2003
ATTTTAAAAT CCTTTAAAAC AACTTTTCAA TTAATATTAT CACACTATTA TCAGATTGTA      2063
ATTAGATGCA AATGAGAGAG CAGTTTAGTT GTTGCATTTT TCGGACACTG GAAAGATTTA      2123
AATGATCAGG AGGGAGTAAC AGAAAGAGCA AGGCTGTTTT TGAAATTCAT TACACTTTCA      2183
CTAGAAGCCC AAACCTCAGC ATTCTGCAAT ATGTAACCAA CATGTCACAA ACAAGCAGCA      2243
TGTAACAGAC TGGCACATGT GCCAGCTGAA TTTAAAATAT AATACTTTTA AAAAGAAAAT      2303
TATTACATCC TTTACATTCA GTTAAGATCA AACCTCACAA AGAGAAATAG AATGTTTGAA      2363
AGGCTATCCC AAAAGACTTT TTTGAATCTG TCATTCACAT ACCCTGTGAA GACAATACTA      2423
TCTACAATTT TTTCAGGATT ATTAAAATCT TCTTTTTTCA CTATCGTAGC TTAAACTCTG      2483
TTTGGTTTTG TCATCTGTAA ATACTTACCT ACATACACTG CATGTAGATG ATTAAATGAG      2543
GGCAGGCCCT GTGCTCATAG CTTTACGATG GAGAGATGCC AGTGACCTCA TAATAAAGAC      2603
TGTGAACTGC CTGGTGCAGT GTCCACATGA CAAAGGGGCA GGTAGCACCC TCTCTCACCC      2663
```

Fig. 2E

```
ATGCTGTGGT TAAAATGGTT TCTAGCATAT GTATAATGCT ATAGTTAAAA TACTATTTTT    2723
CAAAATCATA CAGATTAGTA CATTTAACAG CTACCTGTAA AGCTTATTAC TAATTTTTGT    2783
ATTATTTTTG TAAATAGCCA ATAGAAAAGT TTGCTTGACA TGGTGCTTTT CTTTCATCTA    2843
GAGGCAAAAC TGCTTTTTGA GACCGTAAGA ACCTCTTAGC TTTGTGCGTT CCTGCCTAAT    2903
TTTTATATCT TCTAAGCAAA GTGCCTTAGG ATAGCTTGGG ATGAGATGTG TGTGAAAGTA    2963
TGTACAAGAG AAAACGGAAG AGAGAGGAAA TGAGGTGGGG TTGGAGGAAA CCCATGGGGA    3023
CAGATTCCCA TTCTTAGCCT AACGTTCGTC ATTGCCTCGT CACATCAATG CAAAAGGTCC    3083
TGATTTTGTT CCAGCAAAAC ACAGTGCAAT GTTCTCAGAG TGACTTTCGA AATAAATTGG    3143
GCCCAAGAGC TTTAACTCGG TCTTAAAATA TGCCCAAATT TTTACTTTGT TTTTCTTTTA    3203
ATAGGCTGGG CCACATGTTG GAAATAAGCT AGTAATGTTG TTTTCTGTCA ATATTGAATG    3263
TGATGGTACA GTAAACCAAA ACCCAACAAT GTGGCCAGAA AGAAAGAGCA ATAATAATTA    3323
ATTCACACAC CATATGGATT CTATTTATAA ATCACCCACA AACTTGTTCT TTAATTTCAT    3383
CCCAATCACT TTTTCAGAGG CCTGTTATCA TAGAAGTCAT TTTAGACTCT CAATTTTAAA    3443
TTAATTTTGA ATCACTAATA TTTTCACAGT TTATTAATAT ATTTAATTTC TATTTAAATT    3503
TTAGATTATT TTTATTACCA TGTACTGAAT TTTTACATCC TGATACCCTT TCCTTCTCCA    3563
TGTCAGTATC ATGTTCTCTA ATTATCTTGC CAAATTTTGA AACTACACAC AAAAAGCATA    3623
CTTGCATTAT TTATAATAAA ATTGCATTCA GTGGCTTTTT AAAAAAAATG TTTGATTCAA    3683
AACTTTAACA TACTGATAAG TAAGAAACAA TTATAATTTC TTTACATACT CAAAACCAAG    3743
ATAGAAAAAG GTGCTATCGT TCAACTTCAA AACATGTTTC CTAGTATTAA GGACTTTAAT    3803
ATAGCAACAG ACAAAATTAT TGTTAACATG GATGTTACAG CTCAAAAGAT TTATAAAAGA    3863
TTTTAACCTA TTTTCTCCCT TATTATCCAC TGCTAATGTG GATGTATGTT CAAACACCTT    3923
TTAGTATTGA TAGCTTACAT ATGGCCAAAG GAATACAGTT TATAGCAAAA CATGGGTATG    3983
CTGTAGCTAA CTTTATAAAA GTGTAATATA ACAATGTAAA AAATTATATA TCTGGGAGGA    4043
TTTTTTGGTT GCCTAAAGTG GCTATAGTTA CTGATTTTTT ATTATGTAAG CAAAACCAAT    4103
AAAAATTTAA GTTTTTTTAA CAACTACCTT ATTTTTCACT GTACAGACAC TAATTCATTA    4163
AATACTAATT GATTGTTTAA AAGAAATATA AATGTGACAA GTGGACATTA TTTATGTTAA    4223
ATATACAATT ATCAAGCAAG TATGAAGTTA TTCAATTAAA ATGCCACATT TCTGGTCTCT    4283
GGGAAAAAAA AAAAAAAA                                                 4301
```

HUMAN ENDOTHELIN RECEPTOR

CROSS-REFERENCE TO RELATED APPLICATIONS

This application is a continuation of U.S. application Ser. No. 09/931,157, filed Aug. 16, 2001, now U.S. Pat. No. 6,821,743, which is a divisional of U.S. application Ser. No. 08/121,446, filed Sep. 14, 1993, now U.S. Pat. No. 6,313,276, which is a continuation of U.S. application Ser. No. 07/911,684, filed Jul. 10, 1992 (abandoned), which claims priority to Japanese Patent Application Number 3-172828, filed Jul. 12, 1991, the disclosures of each of which are incorporated herein by reference in their entirety.

BACKGROUND OF THE INVENTION

1. Field of the Invention

The present invention relates to a human endothelin receptor, DNA sequence encoding the receptor, an expression vector carrying the DNA sequence, a transformant comprising the expression vector, and a method for producing a human endothelin receptor from the transformant.

2. Description of the Prior Art

An endothelin receptor (ET-receptor) is a receptor for an endothelin (ET). ET-receptors derived from animals such as bovines and rats have been known. An ET is a peptide present in various tissues in animals and is known as a strong vasoconstrictor. Cloning and sequence analysis of known ET genes have revealed that the ETs comprise three kinds of isopeptides: Endothelin 1 (ET-1), Endothelin 2 (ET-2), and Endothelin 3 (ET-3). Thereafter, it has been found that these ETs are distributed in a wide variety of vascular and non-vascular tissues (Proc. Natl. Acad. Sci. C.S.A. 86, 2863-2867 (1989); Trends in Pharmacol. Sci. 10, 374-378 (1989); and Proc. Natl. Acad. Sci. U.S.A. 87, 2359-2363 (1990)). ET-1 has initially been identified as a strong vasoconstrictive peptide with 21-amino-acid residues produced by porcine vascular endothelial cells (Nature, 332, 411-415 (1988)).

It has previously been shown in vivo that ET-1 and ET-2 are much more strong vasoconstrictors than ET-3, whereas the three ET isopeptides are roughly equipotent in producing the transient vasodilation.

As described above, the analysis of nucleic acid sequences of ETs has revealed that various kinds of ET isopeptides exist. These ET isopeptides are also different in their properties. Therefore, it appears that various subtypes of ET-receptors exist. The existence of various subtypes of ET-receptors has been proved by the radioactive ligand binding studies of Watanabe, H. et al. (Biochem. Biophys. Res. Commun., 161, 1252-1259 (1989)), and Martin, E. R. et al. (J. Biol. Chem. 265, 14044-14049 (1990)). These studies indicate the existence of, at least, two kinds of ET-receptors. One of them has a higher affinity for ET-1 and ET-2 than for ET-3; and the other has an affinity for ET-1, ET-2, and ET-3 with no selectivity.

The ET-receptor is useful as a reagent for measuring the amount of ET or useful in screening for an antagonist of the ET-receptor so as to study agents for the circulatory system. Therefore, there is a demand for a structure analysis of the ET-receptor and effective production of the ET-receptor by means of genetic engineering using the information of this structural analysis.

SUMMARY OF THE INVENTION

The human endothelin receptor of the present invention comprises amino acid sequence from Asp at 21 to Asn at 427 shown in SEQ ID NO: 3.

The human endothelin receptor of the present invention comprises amino acid sequence from Met at 1 to Asn at 427 shown in SEQ ID NO: 3.

The DNA sequence (SEQ ID NO: 1) of the present invention encodes the human endothelin receptor comprising amino acid sequence from Asp at 21 to Asn at 427 shown in SEQ ID NO: 3.

The human endothelin receptor of the present invention comprises amino acid sequence from Glu at 27 to Ser at 442 shown in SEQ ID NO: 4.

The human endothelin receptor of the present invention comprises amino acid sequence from Met at 1 to Ser at 442 shown in SEQ ID NO: 4.

The DNA sequence (SEQ ID NO: 2) of the present invention encodes the human endothelin receptor comprising amino acid sequence from Glu at 27 to Ser at 442 shown in SEQ ID NO: 4.

The expression vector of the present invention comprises the DNA sequence (SEQ ID NO: 1) encoding the human endothelin receptor having amino acid sequence from Asp at 21 to Asn at 427 shown in SEQ ID NO: 3.

The transformant of the present invention is obtained by introducing into a host cell the expression vector comprising the DNA sequence (SEQ ID NO: 1) encoding the human endothelin receptor having amino acid sequence from Asp at 21 to Asn at 427 shown in SEQ ID NO: 3.

The expression vector of the present invention comprises the DNA sequence (SEQ ID NO: 2) encoding the human endothelin receptor having amino acid sequence from Glu at 27 to Ser at 442 shown in SEQ ID NO: 4.

The transformant of the present invention is obtained by introducing into a host cell the expression vector comprising the DNA sequence (SEQ ID NO: 2) encoding the human endothelin receptor having amino acid sequence from Glu at 27 to Ser at 442 shown in SEQ ID NO: 4.

The method for producing a human endothelin receptor of the present invention comprises culturing either one of the above-mentioned transformants and recovering a produced endothelin receptor.

Thus, the invention described herein makes possible the advantage of providing a human ET-receptor, DNA sequence encoding the ET-receptor, an expression vector carrying the DNA sequence, a transformant comprising the expression vector, and a method for producing an ET-receptor from the transformant.

These and other advantages of the present invention will become apparent to those skilled in the art upon reading and understanding the following detailed description with reference to the accompanying figures.

BRIEF DESCRIPTION OF THE DRAWINGS

FIGS. 1A-1E show SEQ ID NO: 1 and SEQ ID NO: 3, a DNA coding sequence and deduced amino acid sequence of an $ET_A$-receptor according to the present invention.

FIGS. 2A-2E show SEQ ID NO: 2 and SEQ ID NO: 4, a DNA coding sequence and deduced amino acid sequence of an $ET_B$-receptor according to the present invention.

DESCRIPTION OF THE PREFERRED EMBODIMENTS

The inventors succeeded in isolating a human ET-receptor cDNA from a cDNA library constructed from poly (A)$^+$ RNA derived from a human placenta, thereby achieving the present invention.

The present invention will be described below in order of the steps involved.

Figure 8:
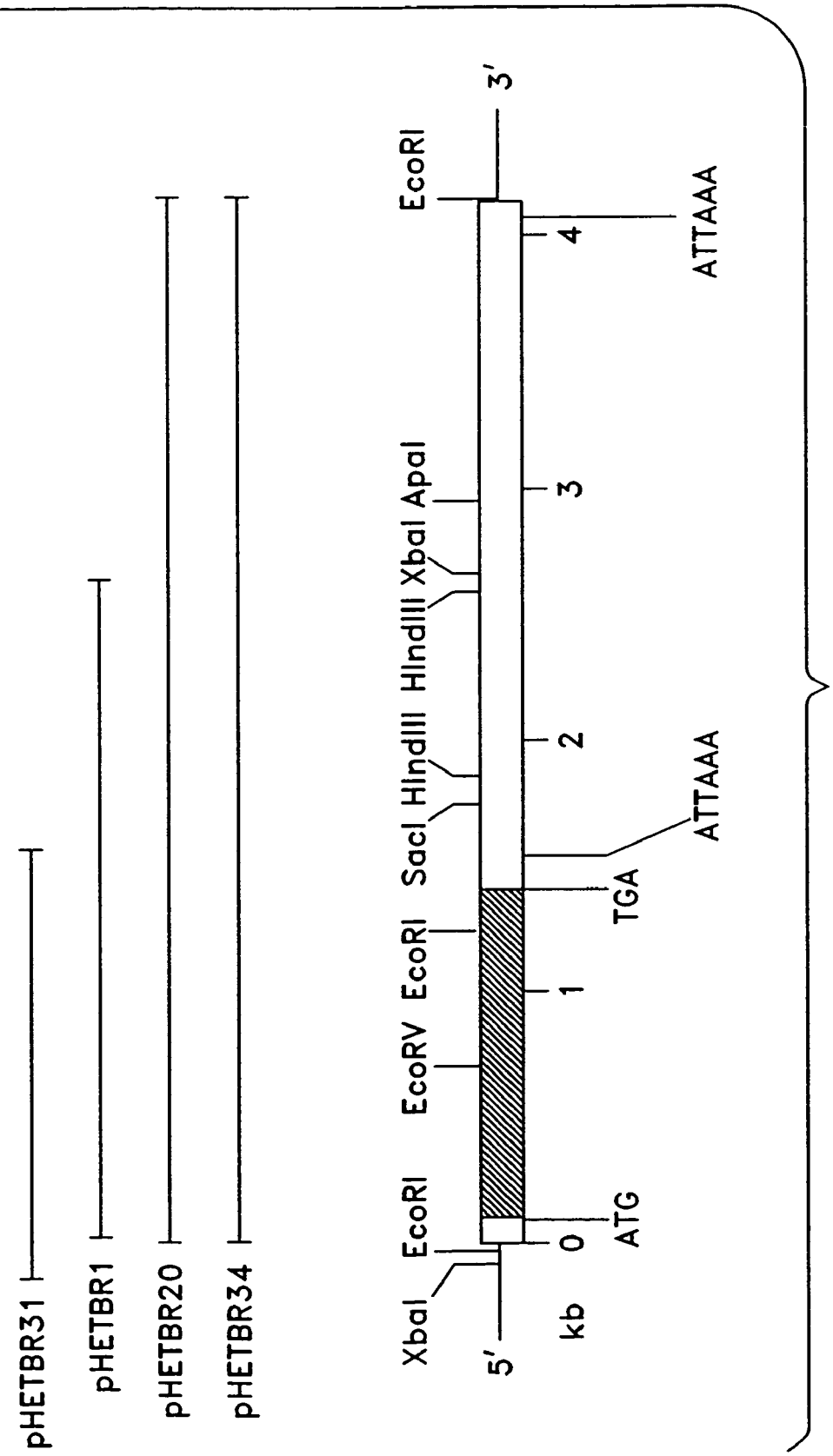
FIG. 8 is a restriction map of DNA sequence of the $ET_B$-receptor according to the present invention.

(I) Sequencing of DNA Encoding a Human ET-Receptor:

First, cDNA prepared from poly(A)$^+$ RNA derived from a human placenta, by using oligo(dT)-primer, is introduced into phage λ ZAPII to construct a cDNA library (Sambrook et al., Molecular Cloning: A Laboratory Manual, Cold Spring Harbor Laboratory, New York (1989)). Then, the cDNA library is screened with the use of DNA fragment of a known ET-receptor as a probe. For example, the cDNA library is screened by hybridizing a probe, an NcoI-EcoRI fragment (960 bp) of DNA encoding a bovine ET-1 receptor, with the cDNA library to obtain positive plasmid clone phETIR. In addition, the cDNA library is hybridized under less stringent conditions to obtain pHETBR1, pHETBR20, pHETBR31 and pHETBR34. cDNA inserts contained in these clones are cut with appropriate restriction enzymes and subcloned, after which these cDNA inserts are sequenced by the dideoxy chain termination method. The nucleic acid sequence of the human ET-receptor thus obtained from phETIR and amino acid sequence corresponding thereto are shown in SEQ ID NO: 1 and SEQ ID NO: 3 in a Sequence Listing. The nucleic acid sequence of the human ET-receptor thus obtained from pHETBR31 and pHETBR34 and amino acid sequence corresponding thereto are shown in SEQ ID NO: 2 and SEQ ID NO: 4 in Sequence Listing. A restriction map of the nucleic acid sequence in SEQ ID NO: 2 is shown in FIG. 8. The positions of 3' termini of the inserts contained in pHETBR31 and pHETBR1 are respectively marked with a double line and a wave line in the sequence of FIG. 2.

The ET-receptor encoded by DNA shown in SEQ ID NO: 1 is a receptor having an affinity for ET-1 and ET-2 ($ET_A$-receptor). The ET-receptor encoded by DNA shown in SEQ ID NO: 2 is a receptor having an affinity (with no selectivity) for both ET-1, ET-2, and ET-3 ($ET_B$-receptor).

(1) DNA Sequence of an ET-Receptor ($ET_A$-Receptor) from phETIR

As shown in SEQ ID NO: 1 and FIG. 1, cDNA contained in the above-mentioned plasmid clone phETIR has a sequence comprising 4,105 nucleic acids. In this nucleic acid sequence, an open reading frame from A at 485 to A at 1768 are constituted, which encodes a 427-amino-acid protein with a molecular weight of 48,726. A sequence adjacent to the initiation codon of the open reading frame is quite consistent with a consensus sequence. A peptide consisting of amino acids from Met corresponding to the initiation codon to the 20th amino acid from Met may be a signal sequence. A 3'-noncoding region contains ATTTA sequence (underlined in the noncoding region of the sequences in FIG. 1), which are related with instability of mRNA. There is a potential polyadenylation signal 22-nucleotides upstream of the poly(A)$^+$ tail (broken underlined in FIG. 1). Hydropathicity analysis of the amino acids constituting the protein encoded by this cDNA indicates that there are seven hydrophobic clusters of 22-26 residues in the protein, each being separated by hydrophilic amino acid sequences. As described above, the protein has seven transmembrane domains, and these domains have an extracellular N tail and a cytoplasmic C tail. The characteristics of this protein are consistent with those of the superfamily of G protein-coupled receptors. These seven transmembrane domains are shown as I to VII in the sequences of FIG. 1.

In the above-mentioned cDNA, there are several potential sites for post-translational modification, and these sites are identical to those of the bovine ET-1 receptor. They include two consensus sequences for N-glycosylation, Asn at 9 and 42 (shown by reverse triangles in FIG. 1); six cysteine residues present on the N terminus side of the cytoplasmic C tail (359, 363, and 365 to 368), one of which may be palmitoylated as in the $\beta_2$-adrenergic receptor; and serine residues that can be phosphorylated with serine/threonine kinases (shown by solid circles in FIG. 1).

The nucleic acid sequence of the open reading frame of cDNA obtained from phETIR is 91.2% homologous to that of bovine ET-1 receptor cDNA.

(2) DNA Sequence of an ET-Receptor ($ET_B$-Receptor) Derived from pHETBR31 and pHETBR34

As shown in SEQ ID NO: 2 and FIG. 2, cDNA obtained from the above two plasmid clones has a sequence comprising 4,301 nucleic acids. In this nucleic acid sequence, an open reading frame from A at 238 to A at 1566 exists, which encodes a 442-amino acid protein with a molecular weight of 49,629. A sequence adjacent to the initiation codon of the open reading frame is quite consistent with a consensus sequence. A peptide consisting of amino acids from Met corresponding to the initiation codon to the 26th amino acid from Met may be a signal sequence. In the same way as in the DNA sequence of the $ET_A$-receptor derived from the above-mentioned phETIR, an ATTTA sequence, seven transmembrane domains (I to VII), a polyadenylation signal, N-glycosylation sites, and serine residues that can be phosphorylated with serine/threonine kinases are shown in the sequences of FIG. 2.

Recently, Sakurai et al. cloned cDNA encoding the ET-receptor of an $ET_B$ type from a rat lung (Nature, 348, 732-735 (1990)). The amino acid sequence of $ET_B$-receptor from a rat is 88% homologous to that of the ET-receptor shown in SEQ ID NO:4, and is 51.9% homologous to that of the ET-receptor shown in SEQ ID NO:3.

The amino acid sequence (SEQ ID NO: 3) of the $ET_A$-receptor shown in SEQ ID NO: 1 is 55% homologous to that of the $ET_B$-receptor shown in SEQ ID NO: 4. The open reading frame of the DNA sequence (SEQ ID NO: 2) encoding the $ET_B$-receptor shown in SEQ ID NO: 4 is 61.1% homologous to that of the bovine $ET_A$-receptor.

(II) Construction of an Expression Vector, a Preparation of a Transformant, and an Expression of an ET-Receptor:

cDNAs encoding the above-mentioned ET-receptors are introduced into appropriate vectors to construct expression vectors. For example, a NotI fragment of the phETIR can be introduced into CDM8 (Nature, 329, 840-842 (1987)), to obtain an expression vector CDM8-phETIR. In the same way, an XbaI fragment of pHETBR34 can be introduced into CDM8 to obtain an expression vector CDM8-pHETBR. These expression vectors can be introduced into appropriate host cells to obtain transformants. For example, a transformant capable of producing an ET-receptor can be obtained by transfecting one of the above-mentioned expression vectors into a COS-7 cell. An ET-receptor is produced by culturing the transformed COS-7 cell under normal conditions. The ET-receptor is expressed (produced) on the cell surface. The produced ET-receptor can be purified by, for example, combinations of various kinds of chromatographies.

The ET-receptor thus produced from a transformant is subjected to a binding assay by the use of known ETs and is confirmed to be an ET-receptor. In addition, it is confirmed which endothelin: ET-1, ET-2, or ET-3 the ET-receptor is specifically bound to.

Figure 3:
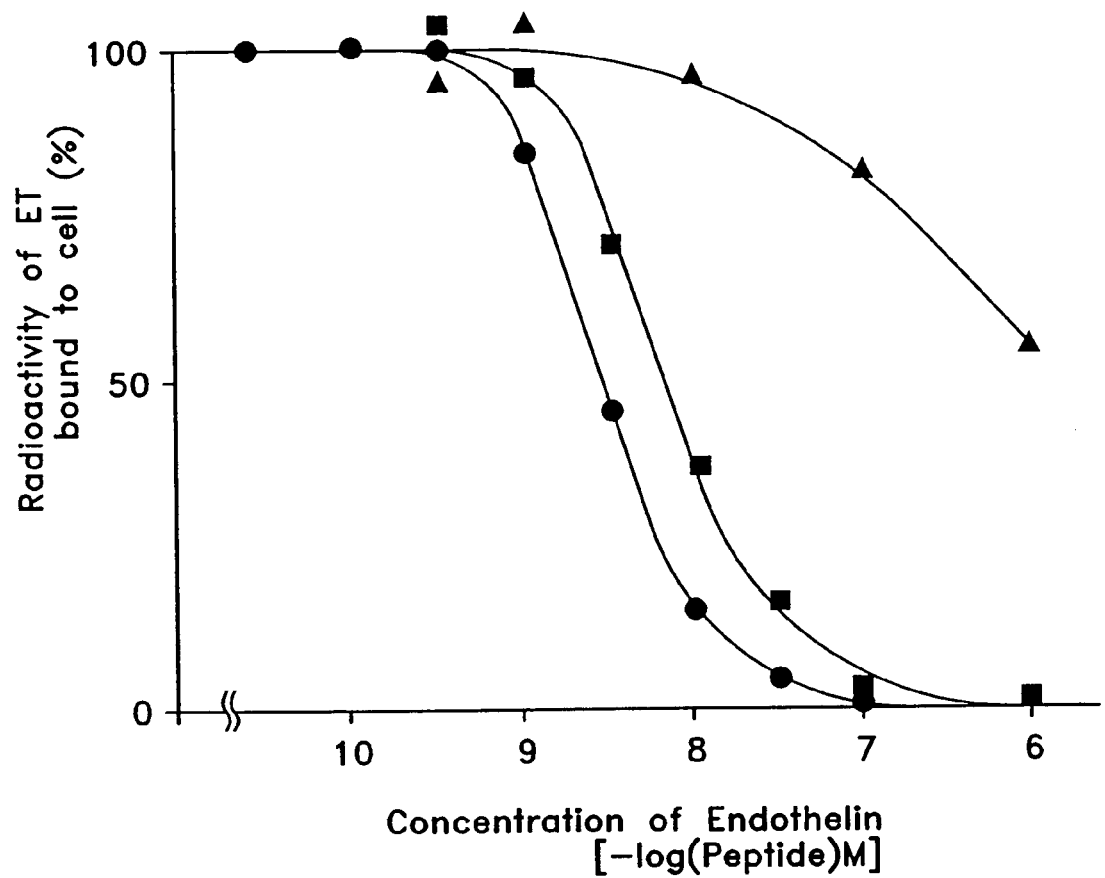
FIG. 3 is a graph showing the results of a binding assay for determining the binding properties of the $ET_A$-receptor to ET-1, ET-2, or ET-3.

For example, first, a predetermined amount of ET-receptor produced by the COS cell transformed with the CDM8-phE-TIR is added to a mixture of a predetermined amount of ET-1 labeled with $^{125}I$ ($^{125}I$-ET-1) and unlabeled ET-1 and to allow to react. Then, the amount of labeled binding complex thus produced is measured. In FIG. 3, the amount of unlabeled ET-1 is plotted on a horizontal axis by changing the concentration thereof in the range of $10^{-10}$ to $10^{-6}$ M, and the radioactivity of an ET-ET-receptor complex (radioactivity of the ET bound to the transformed cell) is plotted on a vertical axis (represented by the symbol ●). Results obtained by performing a competitive assay using unlabeled ET-2 or ET-3 instead of unlabeled ET-1 in the same way as the above are also shown in FIG. 3 (represented by the symbols ■ (ET-2) and ▲ (ET-3)).

The COS-7 cell obtained by transfecting the CDM8, which is a control plasmid, is cultured and is tested in the same way as the above. The binding amount of $^{125}I$-ET-1 is the same level as the amount of non-specific $^{125}I$-ET-1 measured in the presence of an excessive amount of unlabeled ET-1 (the results are not shown). These results indicate that the affinity of the ET-receptor from phETIR according to the present invention for the ET is ET-1 ($IC_{50}$ $3.0 \times 10^{-9}$ M)≧ET-2 ($IC_{50}$ $6.1 \times 10^{-9}$ M)>>ET-3 ($IC_{50}$ $1.0 \times 10^{6}$ M or more), suggesting that this ET-receptor is the $ET_A$-receptor.

Figure 4:
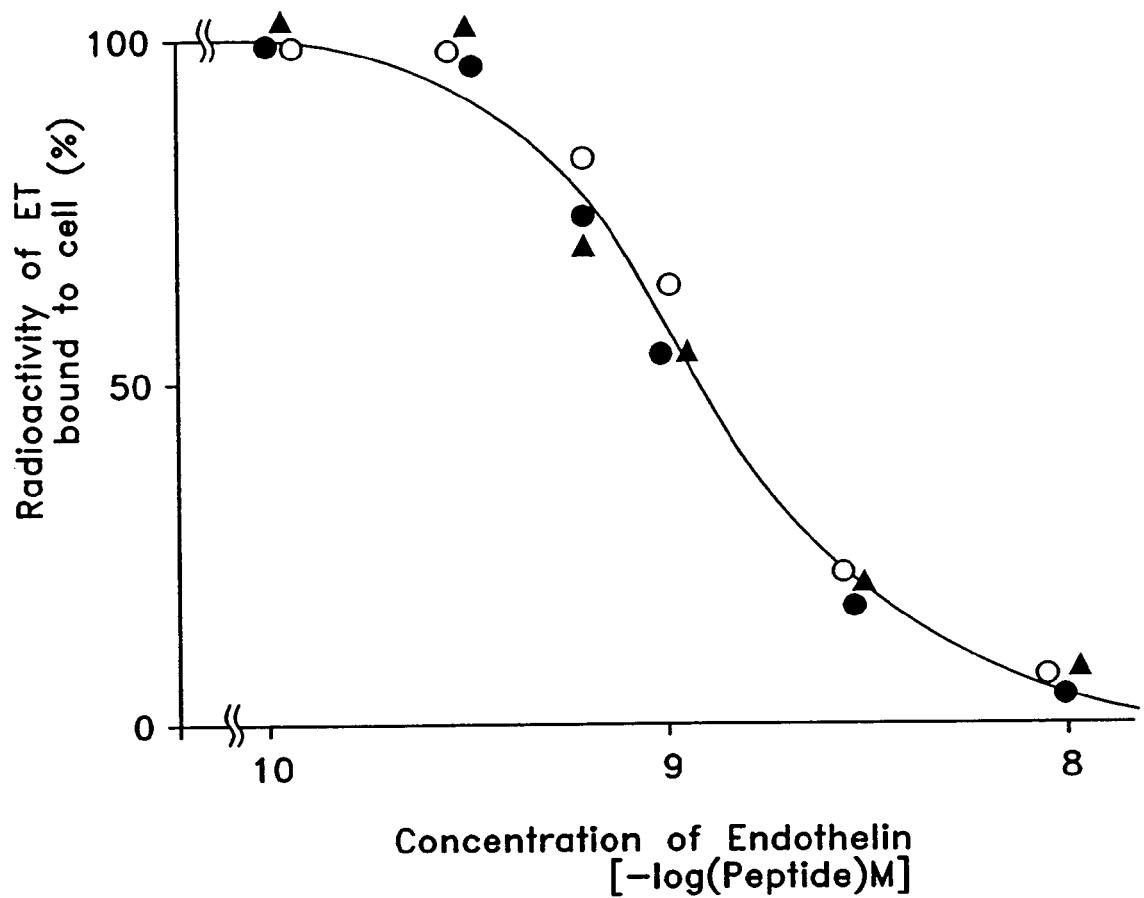
FIG. 4 is a graph showing the results of a binding assay for determining the binding properties of the $ET_B$-receptor to ET-1, ET-2, or ET-3.

The same procedure of binding assay as described above is done for the ET-receptor produced from the COS cell transformed with the CDM8-pHETBR. The results are shown in FIG. 4 (represented by the symbols ● (ET-1), ○ (ET-2), and ▲ (ET-3)). $IC_{50}$ is about $1.0 \times 10^{-9}$ M, suggesting that this ET-receptor is the $ET_B$-receptor.

Figure 5:
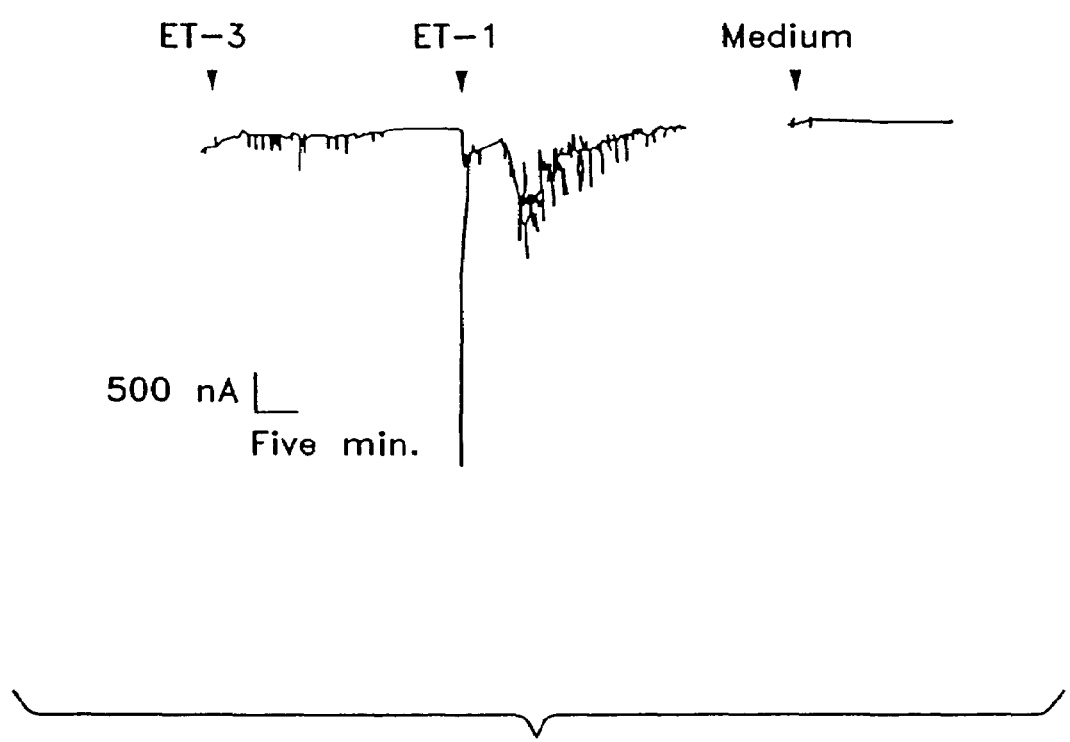
FIG. 5 is a chart recording currents, which are generated at the time that ET-1 or ET-2 is applied to an oocyte of an *Xenopus laevis* injected with mRNA of the $ET_A$-receptor according to the present invention.

(III) Expression of ET-Receptor mRNA in a Cell:

mRNA is synthesized from the cDNA of the ET-receptor of the present invention. When the synthesized mRNA is injected into an appropriate cell, for example, an oocyte of an *Xenopus laevis*, an ET-receptor is expressed in the cell membrane. For example, mRNA is synthesized from cDNA shown in SEQ ID NO: 1 obtained in item (I) with the use of T7RNA polymerase. The synthesized mRNA is injected into an oocyte of an *Xenopus laevis*; as a result, an $ET_A$-receptor is produced in the cell memblene. The production of an $ET_A$-receptor is confirmed by the following procedure. First, the membrane potential of the oocyte injected with mRNA is held at a predetermined value, and then this oocyte is brought into contact with a solution containing ET-1. If the $ET_A$-receptor of the present invention is produced, it is expressed on the cell surface, thus bound to ET-1 present outside the cell. When the $ET_A$-receptor is bound to ET-1, a current flows toward the inside of the cell. Therefore, the production of the ET-receptor of the present invention is confirmed by measuring this current. When the oocyte was brought into contact with a solution containing $10^{-7}$ M ET-1, a current of a large value is confirmed to flow toward the inside of the cell. When the oocyte was brought into contact with a solution containing $10^{-7}$ M ET-2 instead of ET-1, the same value of current is confirmed to flow. In contrast, when the oocyte is brought into contact with a solution containing ET-3, only a small value of current is confirmed to flow. The comparison in current values between ET-1 and ET-3 is shown in FIG. 5. From this result, the $ET_A$-receptor of the present invention has a higher affinity for ET-1 than for ET-3.

(IV) Presence of ET-Receptor mRNA in Various Human Tissues:

(1) Presence of $ET_A$-Receptor mRNA

Figure 6:
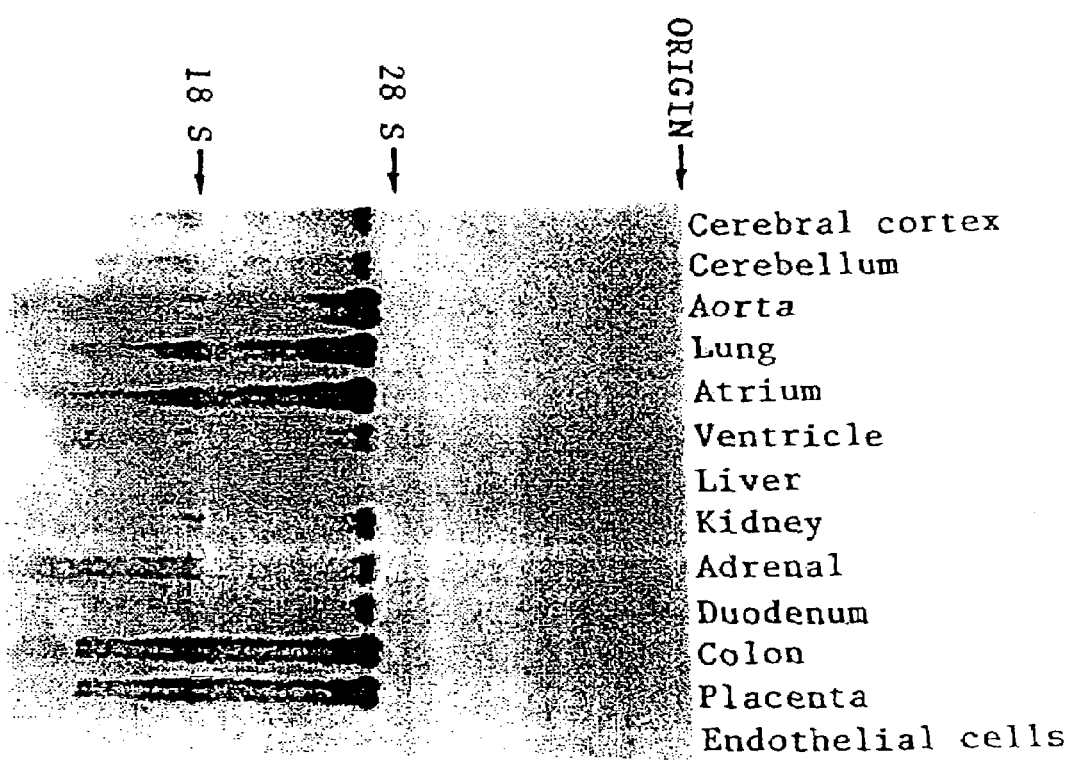
FIG. 6 is a chart of autoradiography showing the results of hybridization of mRNAs isolated from a human tissue with a cDNA fragment of the $ET_A$-receptor according to the present invention.

Northern blot hybridization analysis is conducted on mRNA isolated from various human tissues by using, as a probe, DNA fragment encoding the $ET_A$-receptor of the present invention (EcoRV-EcoRI fragment from phETIR; nucleic acids 739-1564, 826 bp) which is radio-labeled, resulting in a single positive band with a size of 4.3 kb. The results are shown in FIG. 6. The $ET_A$-receptor mRNA of the present invention is present in the aorta at the highest levels; in the lung, atrium, colon and placenta at high levels; and in the cerebral cortex, cerebellum, ventricle, kidney, adrenal and duodenum at moderate levels. A hybridized band is not found in the liver or in the cultured human umbilical vein endothelial cell.

As described above, the $ET_A$-receptor mRNA is present in the circulatory system, especially in the aorta at the highest levels. Since the ET-receptor mRNA is not present in the endothelial cell, the $ET_A$-receptor mRNA is possibly expressed in the vascular smooth muscle cell. Martin et al. describes in J. Biol. Chem. 265, 14044-14049 (1990) that ET-1 and ET-2 inhibit the binding of $^{125}I$-ET-1 to a rat A-10 vascular smooth muscle cell. This result is consistent with the experimental results that the receptor of the present invention is present in the vascular smooth muscle cell. The $ET_A$-receptor of the present invention appears to be a main subtype of the ET-receptor which is expressed in the vascular smooth muscle cell.

In general, it is known that the concentration of ET-1 in plasma is increased due to various diseases such as essential hypertension, vasospastic stenocardia, acute myocardial infarction, chronic renal insufficiency, subarachnoid hemorrhage, and hypoxia. It is conceivable that ET-1 produced in and released from the endothelial cells is bound to an ET-receptor in the vascular smooth muscle cells and acts as a local regulator in maintaining vascular tonus. It is conjectured that the increase in concentration of ET-1 due to the above-mentioned diseases is caused by the collapse of balance between the amount of ET-1 bound to the ET-receptor and the amount of ET-1 released.

(2) Presence of $ET_B$-Receptor mRNA

Figure 7:
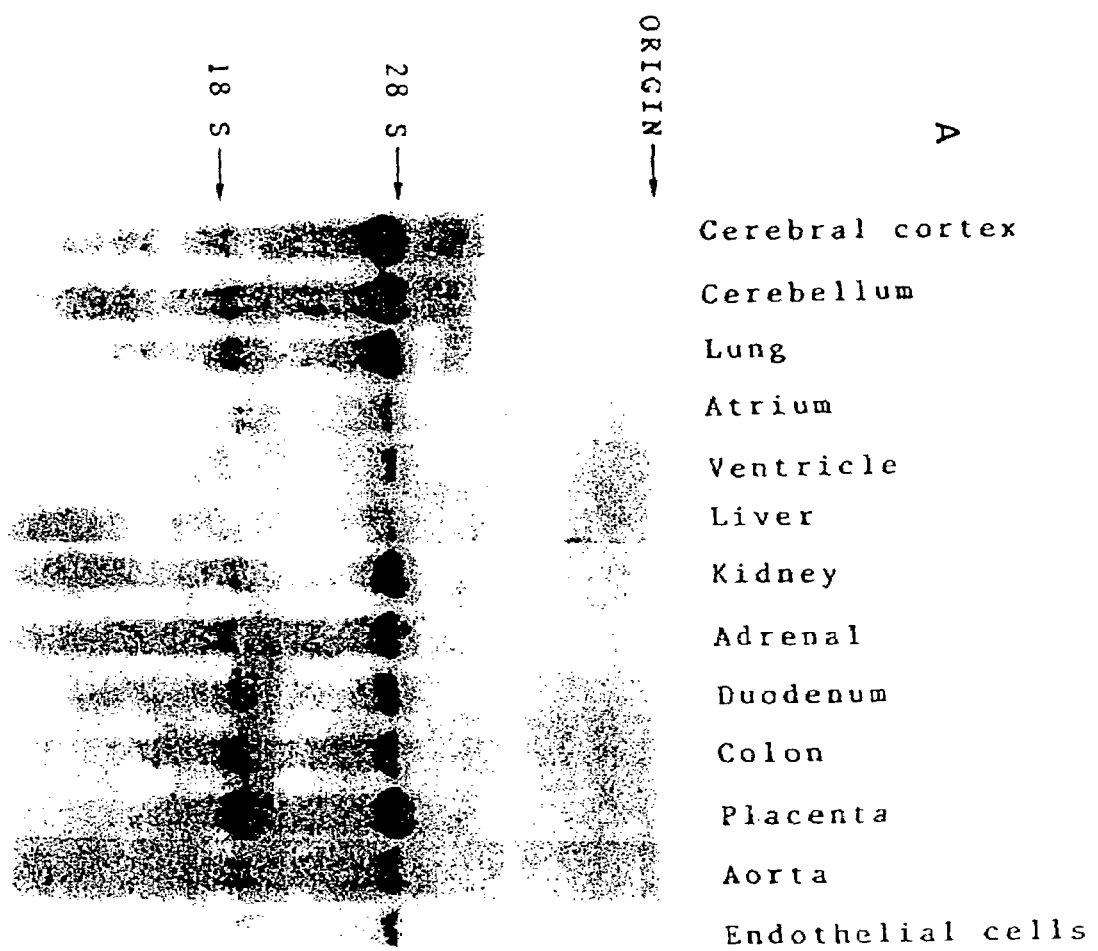
FIG. 7 is a chart of autoradiography showing the results of hybridization of mRNA isolated from a human tissue with a cDNA fragment of the $ET_B$-receptor according to the present invention.

Northern blot hybridization is conducted as described in item (1), by using a probe, 1.2 kb EcoRI fragment, which is derived from pHETBR34 and is radio-labeled, resulting in that a band with a size of 4.3 kb and a band with a size of 1.7 kb are found in various tissues as shown in FIG. 7. It is considered that the plurality of mRNAs is due to the difference in polyadenylation.

It is found that mRNAs with a size of 4.3 kb and 1.7 kb are expressed in the human cerebral cortex and cerebellum at high levels and in the placenta, lung, kidney, adrenal, colon and duodenum at moderate levels.

Example

Hereinafter, the present invention will be described by way of illustrating examples.

(I) Sequencing of DNA Encoding a Human ET-Receptor:

(1) Sequencing of DNA Encoding a Human $ET_A$-Receptor

First, cDNA prepared from poly(A)$^+$ RNA derived from a human placenta, by using oligo(dT)-primer, was introduced into phage λ ZAPII, to construct a cDNA library (Sambrook et al., Molecular Cloning: A laboratory Manual, Cold Spring Harbor Laboratory, New York (1989)). Approximately 1×10$^6$ plaques were screened by using an NcoI-EcoRI fragment (960 bp) of DNA encoding a bovine ET-1 receptor as a probe (Nature, 348, 730-732 (1990)) in the following manner. Filters (Colony/Plaque Screen, du Pont, Wilmington, Del.) to which plaques were replicated were prehybridized for 6 hours in a solution containing 1% SDS, 1 M NaCl, 10% dextran sulfate, 200 μg/ml of yeast tRNA and 250 μg/ml of denatured salmon sperm DNA. Then the filters were hybridized at 65° C. for 18 hours with the probe (NcoI-EcoRI fragment) labeled by random-primed synthesis to the specific activity of 5×10$^8$ cpm/1 μg DNA. The filters were then washed twice (30 min. per wash) in 0.2×SSC (1×SSC is 0.15 M NaCl, 15 mM sodium citrate (pH 7.0)) containing 0.1% SDS at 60° C. The resulting filters were subjected to autoradiography in which the filters were overlayered with Konica enhancing screens and Konica x-ray films (Konica, Tokyo, Japan) and left for 4 hours at −80° C. As a result, a plurality of clones which were hybridized with the probe were found. Fragments of the cDNA insert of phETIR were subcloned into the BLUE-SCRIPT™ plasmid vector (Stratagene, La Jolla, Calif.). Both strands (+−) of the cDNA insert were sequenced by the dideoxy chain termination method using Sequenase (United States Biochemical Corp., Cleveland, Ohio). The nucleic acid sequence and a deduced amino acid sequence of the human ET-receptor obtained from phETIR are shown in SEQ ID NOS: 1 and 3.

(2) Sequencing of DNA Encoding a Human $ET_B$-Receptor

In the same way as in item (1), cDNA prepared from poly(A)$^+$ RNA derived from a human placenta, by using oligo(dT)-primer, was introduced into phage λ ZAPII to construct a cDNA library. The approximately 1×10$^6$ plaques produced were screened using the same probe used in item (1) under conditions different from those in item (1). Filters to which plaques were replicated were immersed in a solution containing 1% SDS, 1 M NaCl, 10% dextran sulfate, 200 μg/ml of yeast RNA and 250 μg/ml of denatured salmon sperm DNA, and the plaques were hybridized with the probe at 65° C. for 18 hours. The filters were then washed twice (30 min. per wash) in 0.5×SSC containing 0.1% SDS at 50° C. The resulting filters were subjected to autoradiography to detect positive clones. Three out of 20 positive clones were clones which became positive even under the highly stringent conditions of hybridization described in item (1) above, and therefore, these three clones are cDNAs of $ET_A$-receptors. Plasmids obtained from the remaining 17 clones were cut with appropriate restriction enzymes and were sequenced by the dideoxy chain termination. As a result, a cDNA sequence shown in SEQ ID NO: 2 was identified from pHETBR31 and pHETBR34.

(II) Construction of an Expression Vector, a Preparation of a Transformant, and an Expression of an ET-Receptor:

(1) $ET_A$-Receptor

A NotI fragment of the phETIR obtained in item (I) was introduced into a CDM8 (Nature, 329, 840-842 (1987)) to obtain an expression vector, CDM8-phETIR. COS-7 cells maintained in Dulbecco's modified Eagle's medium supplemented with 100 U/ml of penicillin and streptomycin and fetal bovine serum (Hazleton, Lenexa, Kans.) were transfected with the CDM8-phETIR, by a calcium phosphate method. Separately, the COS-7 cells were transfected with the control plasmid CDM8. Twenty micrograms of DNA per 100 mm plate were used for transfection. The transfected cells were treated with 20% glycerol for 4 hours after the transfection. Four hours after the glycerol treatment, the cells were harvested from 100 mm plates and 5×10$^4$ cells/well were plated on a 24-well cell culture plate (Corning, Glass Co. Corning, N.Y.).

(2) $ET_B$-Receptor

An XbaI fragment (2.7 kb) of the pHETBR34 obtained in item (I) was introduced into the CDM8 to obtain an expression vector, CDM8-pHETBR. In the same way as described in item (1), this vector was introduced into a COS-7 cell and cultured.

(III) Binding Assay of an ET Receptor Produced from a Transformant to an ET:

$^{125}$I-ET-1 ($^{125}$I-labeled ET-1) (2000 Ci/mmol) was purchased from Amersham (Buckinghamshire, UK). Unlabeled ET-1, ET-2 and ET-3 were purchased from Peptide Institute Inc. (Minoh, Japan).

(1) $ET_A$-Receptor

Binding assays were performed fro a transformant containing CDM8-phETIR obtained in item (II) in a 24-well cell culture plate as follows:

Confluent cells in the wells (48 hours after the glycerol treatment) were washed three times with 1 ml of Hank's balanced salt solution containing 0.1% bovine serum albumin (BSA) (binding medium). A solution containing 50 pM of $^{125}$I-ET-1 and various concentrations ($10^{-10}$ to $10^{-6}$ M) of ET-1 was added to each well. Separately, a solution containing ET-2 or ET-3 instead of ET-1 and a solution containing $^{125}$I-ET-1 alone were prepared, and were respectively added to each well. These solutions added to the wells were incubated at 37° C. for 60 min. Following three washings with 1 ml of ice-cold binding medium, the cells were dissolved in 0.5 ml of 1 N NaOH.

The cell-bound radioactivity was measured by an autogamma counter (Aloka, Tokyo, Japan). The total binding was calculated as follows: (the radioactivity in the absence of unlabeled ET-1, ET-2 or ET-3)—(the radioactivity in the presence of 4×10$^{-7}$ M unlabeled ET-1). All measurements were conducted twice. As a result, the total binding of $^{125}$I-ET-1 was 6900 cpm (background binding in the presence of 4×10$^{-7}$ M ET-1 was 150 cpm). The radioactivity in the presence of ET-1, ET-2, or ET-3 in various concentrations is represented in percent of the total binding (6900 cpm). The results are shown in FIG. 3. It is understood from FIG. 3 that the affinity of the ET-receptor derived from the phETIR of the present invention for ETs is ET-1 (IC$_{50}$ 3.0×10$^{-9}$ M)≧ET-2 (IC$_{50}$ 6.1×10$^{-9}$)>>ET-3 (IC$_{50}$ 1×10$^{-6}$ M or more).

(2) $ET_B$-Receptor

Binding assays were performed in the same way as described in item (1) using a transformant containing the CDM8-pHETBR instead of a transformant containing the CDM8-pHETBR. The results are shown in FIG. 4. In FIG. 4, ○ shows the radioactivity in the presence of ET-2; ● shows the radioactivity in the presence of ET-1; and ▲ shows the radioactivity in the presence of ET-3. It is understood from FIG. 4 that this receptor has almost the same affinity for ET-1, ET-2 and ET-3.

(IV) Expression of ET-Receptor mRNA in a Cell:

Approximately 10 mg of mRNA was synthesized in vitro from phETIR by using T7RNA polymerase in the presence of capping nucleotides. The mRNA thus obtained was pressure-injected into oocytes of an *Xenopus laevis* with a pipette. The oocytes were then incubated in sterile Barth's medium at 20° C. for 3 days. Electro-physiological measurements were performed at 20° C. in an ND96 solution (96 mM NaCl, 2 mM KCl, 1 mM $MgCl_2$, 5 mM Hepes, pH 7.6). Two glass microelectrodes filled with 4 M potassium acetate solution were inserted into an oocyte, and the membrane potential was held at −60 mV. To this oocyte, $1 \times 10^{-7}$ M ET-1, ET-2, or ET-3 desolved in the ND 96 solution containing 0.1% Triton X-100 and 0.1% gelatin were applied.

Twenty seconds after the application of the ET-1 solution, a large inward current was recorded from the oocytes under a holding potential at −60 mV. The chart recorded is shown in FIG. 5. A similar inward current was recorded when $1 \times 10^{-7}$ M ET-2 was applied (not shown). In contrast, a much smaller current was recorded when $1 \times 10^{-7}$ M ET-3 was applied (FIG. 5). The currents caused by the ETs were fluctuating and long-lasting, and were characteristic of $Ca^{2+}$-activated chloride currents. No currents were recorded when the medium alone (ND9 solution containing 0.1% Triton X-100 and 0.1% gelatin) was applied (FIG. 7).

It is understood from the above results that the ET-receptor derived from the phETIR of the present invention has a higher affinity for ET-1 or ET-2 than for ET-3.

(V) Presence of ET-Receptor mRNA in Various Human Tissues:

(1) $ET_A$-Receptor

Among the human tissues used herein, the cerebral cortex, cerebellum, aorta, lung, atrium, liver, kidney, adrenal, duodenum, colon and placenta were obtained from an autopsy or operation. These tissues were weighed, frozen in liquid nitrogen, and stored at −70° C. until used. Human umbilical vein endothelial cells were purchased from Colonetics Corp (San Diego, Calif.), and cultured as described in Lab. Invest. 63, 115-122 (1990).

Total RNA was isolated from each tissue by a guanidinium isocyanate/cesium chloride method. Total RNA was separated on 0.66 M formaldehyde-1% agarose gels (20 µg per lane), and transferred to a nylon membrane (Pall, Glen, Cove, N.Y.) in 20×SSC. Blots were fixed by UV cross-linking and were prehybridized at 65° C. for 12 hours in a solution containing 4×SSC, 10×Denhardt's solution (1×Denhardt's solution is 0.2% polyvinylpyrrolidone, 0.2% BSA, and 0.2% Ficoll), 0.5% SDS, and 250 µg/ml of denatured salmon sperm DNA. The blots were then hybridized at 42° C. for 4 hours in a solution containing 50% formamide, 4×SSC, 5×Denhardt's solution, 0.5% SDS, 10% dextran sulfate, 250 µg/ml of denatured salmon sperm DNA, and the radio-labeled EcoRV-EcoRI fragment of the insert of phETIR (826 bp; used as a probe). The probe was labeled by random-primed synthesis to the specific activity of $1 \times 10^{-9}$ cpm/µg DNA. The blots were washed twice at room temperature (30 min. per wash): once at 60° C. in a solution containing 2×SSC and 0.1% SDS (30 min. per wash) and twice at 60° C. in a solution containing 0.1× SSC and 0.1% SDS (15 min. per wash).

The resulting blots were subjected to autoradiography in which filters carrying blots were overlayered with Konica enhancing screens and Kodak X-OMAT™ AR film (Kodak, Corp. Rochester, N.Y.) and left for 3 days at −70° C. The results are shown in FIG. 6. A single band with a size of 4.3 kb is located in various tissues, suggesting that mRNAs of the ET-receptor of the present invention are present in various tissues. In particular, the mRNAs are present in the aorta at the highest levels; in the lung, atrium, colon, and placenta at high levels; and in the cerebral cortex, cerebellum, ventricle, kidney, adrenal, and duodenum at moderate levels. A hybridized band is not found in the liver and in the cultured human umbilical vein endothelial cell.

(2) $ET_B$-Receptor

Autoradiography was performed in the same way as described in item (1) above, except that the radio-labeled EcoRI fragment (1.2 kb) of the insert of pHETBR34 was used as a probe instead of the radio-labeled EcoRV-EcoRI fragment of the insert of pHETIR. The results are shown in FIG. 7. As shown in FIG. 7, bands with a size of about 4.3 kb and 1.7 kb are located. It is understood that the $ET_B$-receptor mRNA is present in the cerebral cortex and cerebellum at high levels. In addition, unlike the $ET_A$-receptor, the $ET_B$-receptor mRNA is present in the umbilical vein endothelial cell.

As described above, according to the present invention, a novel human endothelin receptor, DNA sequence encoding the receptor, an expression vector having the DNA sequence, a transformant comprising the expression vector, and a method for producing a human endothelin receptor from the transformant are provided. The receptor shown in SEQ ID NO: 1 is an $ET_A$-receptor which has an affinity for ET-1 and ET-2, especially the affinity for ET-1 being stronger. The receptor shown in SEQ ID NO: 2 is an $ET_B$-receptor which has an affinity for ET-1, ET-2 and ET-3 (with no selectivity). Thus, it is the first time that both an $ET_A$-receptor and an $ET_B$-receptor are found in a specific mammal. The ET-receptors obtained are useful as an agent for measuring the amount of ET or useful in screening for an antagonist of the ET-receptors so as to study agents for the circulatory system.

Various other modifications will be apparent to and can be readily made by those skilled in the art without departing from the scope and spirit of this invention. Accordingly, it is not intended that the scope of the claims appended hereto be limited to the description as set forth herein, but rather that the claims be broadly construed.

The following specific sequence information and descriptions are provided in order to comply with the formal requirements of the submission of sequence data to the United States Patent and Trademark Office and are not intended to limit the scope of what the inventors regard as their invention. Variations in sequences which become apparent to those skilled in the art upon review of this disclosure and which are encompassed by the attached claims are intended to be within the scope of the present invention. Further, it should be noted that efforts have been made to insure accuracy with respect to the specific sequences and characteristic description information describing such sequences, but some experimental error and/or deviation should be accounted for.

What is claimed is:

1. An isolated human endothelin receptor encoded by a polynucleotide comprising nucleotides 545 to 1765 of SEQ ID NO: 1.

2. An isolated human endothelin receptor comprising amino encoded by a polynucleotide comprising nucleotides 485 to 1765 of SEQ ID NO: 1.

3. An isolated human endothelin receptor comprising amino acid residues 21 to 427 of SEQ ID NO: 3.

4. An isolated human endothelin receptor comprising the amino acid sequence of SEQ ID NO: 3.

* * * * *

SEQUENCE LISTING

<160> NUMBER OF SEQ ID NOS: 2

<210> SEQ ID NO 1
<211> LENGTH: 4105
<212> TYPE: DNA
<213> ORGANISM: Homo Sapiens
<220> FEATURE:
<221> NAME/KEY: CDS
<222> LOCATION: (485)...(1768)
<220> FEATURE:
<221> NAME/KEY: sig_peptide
<222> LOCATION: (485)...(544)
<220> FEATURE:
<221> NAME/KEY: mat_peptide
<222> LOCATION: (545)...(1768)

<400> SEQUENCE: 1

```
gaattcgcgg ccgcctcttg cggtcccaga gtggagtgga aggtctggag ctttgggagg     60
agacggggag gacagactgg aggcgtgttc ctccggagtt ttcttttcg tgcgagccct    120 cgcgcgcgcg tacagtcatc ccgctggtct gacgattgtg gagaggcggt ggagaggctt    180
catccatccc acccggtcgt cgccggggat tggggtccca gcgacacctc cccgggagaa    240
gcagtgccca ggaagttttc tgaagccggg gaagctgtgc agccgaagcc gccgccgcgc    300
cggagcccgg gacaccggcc accctccgcg ccacccaccc tcgctttctc cggcttcctc    360
tggcccaggc gccgcgcgga cccggcagct gtctgcgcac gccgagctcc acggtgaaaa    420
aaaaagtgaa ggtgtaaaag cagcacaagt gcaataagag atatttcctc aaatttgcct    480
```

| caag atg gaa acc ctt tgc ctc agg gca tcc ttt tgg ctg gca ctg gtt | 529 |
|---|---|
| Met Glu Thr Leu Cys Leu Arg Ala Ser Phe Trp Leu Ala Leu Val | |
| -20 -15 -10 | |

| gga tgt gta atc agt gat aat cct gag aga tac agc aca aat cta agc | 577 |
|---|---|
| Gly Cys Val Ile Ser Asp Asn Pro Glu Arg Tyr Ser Thr Asn Leu Ser | |
| -5 1 5 10 | |

| aat cat gtg gat gat ttc acc act ttt cgt ggc aca gag ctc agc ttc | 625 |
|---|---|
| Asn His Val Asp Asp Phe Thr Thr Phe Arg Gly Thr Glu Leu Ser Phe | |
| 15 20 25 | |

| ctg gtt acc act cat caa ccc act aat ttg gtc cta ccc agc aat ggc | 673 |
|---|---|
| Leu Val Thr Thr His Gln Pro Thr Asn Leu Val Leu Pro Ser Asn Gly | |
| 30 35 40 | |

| tca atg cac aac tat tgc cca cag cag act aaa att act tca gct ttc | 721 |
|---|---|
| Ser Met His Asn Tyr Cys Pro Gln Gln Thr Lys Ile Thr Ser Ala Phe | |
| 45 50 55 | |

| aaa tac att aac act gtg ata tct tgt act att ttc atc gtg gga atg | 769 |
|---|---|
| Lys Tyr Ile Asn Thr Val Ile Ser Cys Thr Ile Phe Ile Val Gly Met | |
| 60 65 70 75 | |

| gtg ggg aat gca act ctg ctc agg atc att tac cag aac aaa tgt atg | 817 |
|---|---|
| Val Gly Asn Ala Thr Leu Leu Arg Ile Ile Tyr Gln Asn Lys Cys Met | |
| 80 85 90 | |

| agg aat ggc ccc aac gcg ctg ata gcc agt ctt gcc ctt gga gac ctt | 865 |
|---|---|
| Arg Asn Gly Pro Asn Ala Leu Ile Ala Ser Leu Ala Leu Gly Asp Leu | |
| 95 100 105 | |

| atc tat gtg gtc att gat ctc cct atc aat gta ttt aag ctg ctg gct | 913 |
|---|---|
| Ile Tyr Val Val Ile Asp Leu Pro Ile Asn Val Phe Lys Leu Leu Ala | |
| 110 115 120 | |

| ggg cgc tgg cct ttt gat cac aat gac ttt ggc gta ttt ctt tgc aag | 961 |
|---|---|
| Gly Arg Trp Pro Phe Asp His Asn Asp Phe Gly Val Phe Leu Cys Lys | |
| 125 130 135 | |

| ctg ttc ccc ttt ttg cag aag tcc tcg gtg ggg atc acc gtc ctc aac | 1009 |
|---|---|
| Leu Phe Pro Phe Leu Gln Lys Ser Ser Val Gly Ile Thr Val Leu Asn | |

```
                  140               145               150               155
ctc tgc gct ctt agt gtt gac agg tac aga gca gtt gcc tcc tgg agt              1057
Leu Cys Ala Leu Ser Val Asp Arg Tyr Arg Ala Val Ala Ser Trp Ser
            160               165               170 cgt gtt cag gga att ggg att cct ttg gta act gcc att gaa att gtc              1105
Arg Val Gln Gly Ile Gly Ile Pro Leu Val Thr Ala Ile Glu Ile Val
        175               180               185 tcc atc tgg atc ctg tcc ttt atc ctg gcc att cct gaa gcg att ggc              1153
Ser Ile Trp Ile Leu Ser Phe Ile Leu Ala Ile Pro Glu Ala Ile Gly
        190               195               200 ttc gtc atg gta ccc ttt gaa tat agg ggt gaa cag cat aaa acc tgt              1201
Phe Val Met Val Pro Phe Glu Tyr Arg Gly Glu Gln His Lys Thr Cys
205               210               215 atg ctc aat gcc aca tca aaa ttc atg gag ttc tac caa gat gta aag              1249
Met Leu Asn Ala Thr Ser Lys Phe Met Glu Phe Tyr Gln Asp Val Lys
220               225               230               235 gac tgg tgg ctc ttc ggg ttc tat ttc tgt atg ccc ttg gtg tgc act              1297
Asp Trp Trp Leu Phe Gly Phe Tyr Phe Cys Met Pro Leu Val Cys Thr
            240               245               250 gcg atc ttc tac acc ctc atg act tgt gag atg ttg aac aga agg aat              1345
Ala Ile Phe Tyr Thr Leu Met Thr Cys Glu Met Leu Asn Arg Arg Asn
        255               260               265 ggc agc ttg aga att gcc ctc agt gaa cat ctt aag cag cgt cga gaa              1393
Gly Ser Leu Arg Ile Ala Leu Ser Glu His Leu Lys Gln Arg Arg Glu
        270               275               280 gtg gca aaa aca gtt ttc tgc ttg gtt gta att ttt gct ctt tgc tgg              1441
Val Ala Lys Thr Val Phe Cys Leu Val Val Ile Phe Ala Leu Cys Trp
285               290               295 ttc cct ctt cac tta agc cgt ata ttg aag aaa act gtg tat aac gaa              1489
Phe Pro Leu His Leu Ser Arg Ile Leu Lys Lys Thr Val Tyr Asn Glu
300               305               310               315 atg gac aag aac cga tgt gaa tta ctt agt ttc tta ctg ctc atg gat              1537
Met Asp Lys Asn Arg Cys Glu Leu Leu Ser Phe Leu Leu Leu Met Asp
            320               325               330 tac atc ggt att aac ttg gca acc atg aat tca tgt ata aac ccc ata              1585
Tyr Ile Gly Ile Asn Leu Ala Thr Met Asn Ser Cys Ile Asn Pro Ile
        335               340               345 gct ctg tat ttt gtg agc aag aaa ttt aaa aat tgt ttc cag tca tgc              1633
Ala Leu Tyr Phe Val Ser Lys Lys Phe Lys Asn Cys Phe Gln Ser Cys
        350               355               360 ctc tgc tgc tgc tgt tac cag tcc aaa agt ctg atg acc tcg gtc ccc              1681
Leu Cys Cys Cys Cys Tyr Gln Ser Lys Ser Leu Met Thr Ser Val Pro
365               370               375 atg aac gga aca agc atc cag tgg aag aac cac gat caa aac aac cac              1729
Met Asn Gly Thr Ser Ile Gln Trp Lys Asn His Asp Gln Asn Asn His
            380               385               390               395 aac aca gac cgg agc agc cat aag gac agc atg aac tga ccacccttag              1778
Asn Thr Asp Arg Ser Ser His Lys Asp Ser Met Asn *
        400               405 aagcactcct cggtactccc ataatcctct cggagaaaaa aatcacaagg caactgtgac           1838
tccgggaatc tcttctctga tccttcttcc ttaattcact cccacaccca agaagaaatg           1898
ctttccaaaa ccgcaaggta gactggttta tccacccaca acatctacga atcgtacttc           1958
tttaattgat ctaatttaca tattctgcgt gttgtattca gcactaaaaa atggtgggag           2018
ctgggggaga atgaagactg ttaaatgaaa ccagaaggat atttactact tttgcatgaa           2078
aatagagctt tcaagtacat ggctagcttt tatggcagtt ctggtgaatg ttcaatggga           2138
actggtcacc atgaaacttt agagattaac gacaagattt tctactttt ttaagtgatt            2198
```

```
ttttgtcctt cagccaaaca caatatgggc tcaggtcact tttatttgaa atgtcatttg    2258
gtgccagtat ttttaactg cataatagcc taacatgatt atttgaactt atttacacat    2318
agtttgaaaa aaaaaagaca aaaatagtat tcaggtgagc aattagatta gtattttcca    2378
cgtcactatt tatttttta aaacacaaat tctaaagcta caacaaatac tacaggccct    2438
taaagcacag tctgatgaca catttggcag tttaatagat gttactcaaa gaatttttta    2498
agaactgtat tttattttt aaatggtgtt ttattacaag ggaccttgaa catgttttgt    2558
atgttaaatt caaagtaat gcttcaatca gatagttctt tttcacaagt tcaatactgt    2618
ttttcatgta aattttgtat gaaaaatcaa tgtcaagtac caaaatgtta atgtatgtgt    2678
catttaactc tgcctgagac tttcagtgca ctgtatatag aagtctaaaa cacacctaag    2738
agaaaaagat cgaattttc agatgattcg gaaattttca ttcaggtatt tgtaatagtg    2798
acatatatat gtatatacat atcacctcct attctcttaa tttttgttaa aatgttaact    2858
ggcagtaagt cttttttgat cattccctt tccatatagg aaacataatt ttgaagtggc    2918
cagatgagtt tatcatgtca gtgaaaaata attacccaca aatgccacca gtaacttaac    2978
gattcttcac ttcttggggt tttcagtatg aacctaactc cccaccccaa catctccctc    3038
ccacattgtc accatttcaa agggcccaca gtgacttttg ctgggcattt tcccagatgt    3098
ttacagactg tgagtacagc agaaaatctt ttactagtgt gtgtgtgtat atatataaac    3158
aattgtaaat ttcttttagc ccatttttct agactgtctc tgtggaatat atttgtgtgt    3218
gtgatatatg catgtgtgtg atggtatgta tggatttaat ctaatctaat aattgtgccc    3278
cgcagttgtg ccaaagtgca tagtctgagc taaaatctag gtgattgttc atcatgacaa    3338
cctgcctcag tccattttaa cctgtagcaa ccttctgcat tcataaatct tgtaatcatg    3398
ttaccattac aaatgggata taagaggcag cgtgaaagca gatgagctgt ggactagcaa    3458
tatagggttt tgtttggttg gttggtttga taaagcagta tttggggtca tattgtttcc    3518
tgtgctggag caaaagtcat tacactttga agtattatat tgttcttatc ctcaattcaa    3578
tgtggtgatg aaattgccag gttgtctgat atttcttca gacttcgcca gacagattgc    3638
tgataataaa ttaggtaaga aatttgttg ggccatattt taggacaggt aaaataacat    3698
caggttccag ttgcttgaat tgcaaggcta agaagtactg cccttttgtg tgttagcagt    3758
caaatctatt attccactgg cgcatcatat gcagtgatat atgcctataa tataagccat    3818
aggttcacac cattttgttt agacaattgt ctttttttca agatgctttg tttctttcat    3878
atgaaaaaaa tgcattttat aaattcagaa agtcatagat ttctgaaggc gtcaacgtgc    3938
attttattta tggactggta agtaactgtg gtttactagc aggaatattt ccaatttcta    3998
cctttactac atcttttcaa caagtaactt tgtagaaatg agccagaagc caaggccctg    4058
agttggcagt ggcccataag tgtaaaataa aagtttacag aaacctt                 4105

<210> SEQ ID NO 2
<211> LENGTH: 4301
<212> TYPE: DNA
<213> ORGANISM: Homo Sapiens
<220> FEATURE:
<221> NAME/KEY: CDS
<222> LOCATION: (238)...(1566)

<400> SEQUENCE: 2
gagacattcc ggtgggggac tctggccagc ccgagcaacg tggatcctga gagcactccc      60
aggtaggcat ttgccccggt gggacgcctt gccagagcag tgtgtggcag gccccgtgg     120
```

-continued

```
aggatcaaca cagtggctga acactgggaa ggaactggta cttggagtct ggacatctga      180
aacttggctc tgaaactgcg gagcggccac cggacgcctt ctggagcagg tagcagc atg    240
                                                                Met
                                                                 1 cag ccg cct cca agt ctg tgc gga cgc gcc ctg gtt gcg ctg gtt ctt        288
Gln Pro Pro Pro Ser Leu Cys Gly Arg Ala Leu Val Ala Leu Val Leu
             5                  10                  15 gcc tgc ggc ctg tcg cgg atc tgg gga gag gag aga ggc ttc ccg cct        336
Ala Cys Gly Leu Ser Arg Ile Trp Gly Glu Glu Arg Gly Phe Pro Pro
 20              25                  30 gac agg gcc act ccg ctt ttg caa acc gca gag ata atg acg cca ccc        384
Asp Arg Ala Thr Pro Leu Leu Gln Thr Ala Glu Ile Met Thr Pro Pro
 35                  40                  45 act aag acc tta tgg ccc aag ggt tcc aac gcc agt ctg gcg cgg tcg        432
Thr Lys Thr Leu Trp Pro Lys Gly Ser Asn Ala Ser Leu Ala Arg Ser
 50              55                  60                  65 ttg gca cct gcg gag gtg cct aaa gga gac agg acg gca gga tct ccg        480
Leu Ala Pro Ala Glu Val Pro Lys Gly Asp Arg Thr Ala Gly Ser Pro
             70                  75                  80 cca cgc acc atc tcc cct ccc ccg tgc caa gga ccc atc gag atc aag        528
Pro Arg Thr Ile Ser Pro Pro Pro Cys Gln Gly Pro Ile Glu Ile Lys
 85                  90                  95 gag act ttc aaa tac atc aac acg gtt gtg tcc tgc ctt gtg ttc gtg        576
Glu Thr Phe Lys Tyr Ile Asn Thr Val Val Ser Cys Leu Val Phe Val
100                 105                 110 ctg ggg atc atc ggg aac tcc aca ctt ctg aga att atc tac aag aac        624
Leu Gly Ile Ile Gly Asn Ser Thr Leu Leu Arg Ile Ile Tyr Lys Asn
115                 120                 125 aag tgc atg cga aac ggt ccc aat atc ttg atc gcc agc ttg gct ctg        672
Lys Cys Met Arg Asn Gly Pro Asn Ile Leu Ile Ala Ser Leu Ala Leu
130                 135                 140                 145 gga gac ctg ctg cac atc gtc att gac atc cct atc aat gtc tac aag        720
Gly Asp Leu Leu His Ile Val Ile Asp Ile Pro Ile Asn Val Tyr Lys
            150                 155                 160 ctg ctg gca gag gac tgg cca ttt gga gct gag atg tgt aag ctg gtg        768
Leu Leu Ala Glu Asp Trp Pro Phe Gly Ala Glu Met Cys Lys Leu Val
            165                 170                 175 cct ttc ata cag aaa gcc tcc gtg gga atc act gtg ctg agt cta tgt        816
Pro Phe Ile Gln Lys Ala Ser Val Gly Ile Thr Val Leu Ser Leu Cys
180                 185                 190 gct ctg agt att gac aga tat cga gct gtt gct tct tgg agt aga att        864
Ala Leu Ser Ile Asp Arg Tyr Arg Ala Val Ala Ser Trp Ser Arg Ile
195                 200                 205 aaa gga att ggg gtt cca aaa tgg aca gca gta gaa att gtt ttg att        912
Lys Gly Ile Gly Val Pro Lys Trp Thr Ala Val Glu Ile Val Leu Ile
210                 215                 220                 225 tgg gtg gtc tct gtg gtt ctg gct gtc cct gaa gcc ata ggt ttt gat        960
Trp Val Val Ser Val Val Leu Ala Val Pro Glu Ala Ile Gly Phe Asp
            230                 235                 240 ata att acg atg gac tac aaa gga agt tat ctg cga atc tgc ttg ctt       1008
Ile Ile Thr Met Asp Tyr Lys Gly Ser Tyr Leu Arg Ile Cys Leu Leu
            245                 250                 255 cat ccc gtt cag aag aca gct ttc atg cag ttt tac aag aca gca aaa       1056
His Pro Val Gln Lys Thr Ala Phe Met Gln Phe Tyr Lys Thr Ala Lys
260                 265                 270 gat tgg tgg ctg ttc agt ttc tat ttc tgc ttg cca ttg gcc atc act       1104
Asp Trp Trp Leu Phe Ser Phe Tyr Phe Cys Leu Pro Leu Ala Ile Thr
275                 280                 285
```

```
gca ttt ttt tat aca cta atg acc tgt gaa atg ttg aga aag aaa agt    1152
Ala Phe Phe Tyr Thr Leu Met Thr Cys Glu Met Leu Arg Lys Lys Ser
290                 295                 300                 305 ggc atg cag att gct tta aat gat cac cta aag cag aga cgg gaa gtg    1200
Gly Met Gln Ile Ala Leu Asn Asp His Leu Lys Gln Arg Arg Glu Val
        310                 315                 320 gcc aaa acc gtc ttt tgc ctg gtc ctt gtc ttt gcc ctc tgc tgg ctt    1248
Ala Lys Thr Val Phe Cys Leu Val Leu Val Phe Ala Leu Cys Trp Leu
325                 330                 335 ccc ctt cac ctc agc agg att ctg aag ctc act ctt tat aat cag aat    1296
Pro Leu His Leu Ser Arg Ile Leu Lys Leu Thr Leu Tyr Asn Gln Asn
340                 345                 350 gat ccc aat aga tgt gaa ctt ttg agc ttt ctg ttg gta ttg gac tat    1344
Asp Pro Asn Arg Cys Glu Leu Leu Ser Phe Leu Leu Val Leu Asp Tyr
355                 360                 365 att ggt atc aac atg gct tca ctg aat tcc tgc att aac cca att gct    1392
Ile Gly Ile Asn Met Ala Ser Leu Asn Ser Cys Ile Asn Pro Ile Ala
370                 375                 380                 385 ctg tat ttg gtg agc aaa aga ttc aaa aac tgc ttt aag tca tgc tta    1440
Leu Tyr Leu Val Ser Lys Arg Phe Lys Asn Cys Phe Lys Ser Cys Leu
        390                 395                 400 tgc tgc tgg tgc cag tca ttt gaa gaa aaa cag tcc ttg gag gaa aag    1488
Cys Cys Trp Cys Gln Ser Phe Glu Glu Lys Gln Ser Leu Glu Glu Lys
405                 410                 415 cag tcg tgc tta aag ttc aaa gct aat gat cac gga tat gac aac ttc    1536
Gln Ser Cys Leu Lys Phe Lys Ala Asn Asp His Gly Tyr Asp Asn Phe
420                 425                 430 cgt tcc agt aat aaa tac agc tca tct tga aagaagaact attcactgta      1586
Arg Ser Ser Asn Lys Tyr Ser Ser Ser *
435                 440 tttcattttc tttatattgg accgaagtca ttaaaacaaa atgaaacatt tgccaaaaca  1646
aaacaaaaaa ctatgtattt gcacagcaca ctattaaaat attaagtgta attattttaa  1706
cactcacagc tacatatgac attttatgag ctgtttacgg catggaaaga aaatcagtgg  1766
gaattaagaa agcctcgtcg tgaaagcact taatttttta cagttagcac ttcaacatag  1826
ctcttaacaa cttccaggat attcacacaa cacttaggct taaaaatgag ctcactcaga  1886
atttctattc tttctaaaaa gagatttatt tttaaatcaa tgggactctg atataaagga  1946
agaataagtc actgtaaaac agaactttta aatgaagctt aaattactca atttaaaatt  2006
ttaaaatcct ttaaaacaac ttttcaatta atattatcac actattatca gattgtaatt  2066
agatgcaaat gagagagcag tttagttgtt gcattttcg gacactggaa acatttaaat   2126
gatcaggagg gagtaacaga aagagcaagg ctgtttttga aaatcattac actttcacta  2186
gaagcccaaa cctcagcatt ctgcaatatg taaccaacat gtcacaaaca agcagcatgt  2246
aacagactgg cacatgtgcc agctgaattt aaaatataat acttttaaaa agaaaattat  2306
tacatccttt acattcagtt aagatcaaac ctcacaaaga gaaatagaat gtttgaaagg  2366
ctatcccaaa agactttttt gaatctgtca ttcacatacc ctgtgaagac aatactatct  2426
acaatttttt caggattatt aaaatcttct ttttcacta tcgtagctta aactctgttt    2486
ggttttgtca tctgtaaata cttacctaca tacactgcat gtagatgatt aaatgagggc   2546
aggccctgtg ctcatagctt tacgatggag agatgccagt gacctcataa taagactgt    2606 gaactgcctg gtgcagtgtc cacatgacaa aggggcaggt agcaccctct ctcacccatg   2666
ctgtggttaa aatggtttct agcatatgta taatgctata gttaaaatac tattttcaa    2726 aatcatacag attagtacat ttaacagcta cctgtaaagc ttattactaa tttttgtatt   2786
```

-continued

```
attttgtaa   atagccaata  gaaaagtttg  cttgacatgg  tgcttttctt  tcatctagag   2846
gcaaaactgc  tttttgagac  cgtaagaacc  tcttagcttt  gtgcgttcct  gcctaatttt   2906
tatatcttct  aagcaaagtg  ccttaggata  gcttgggatg  agatgtgtgt  gaaagtatgt   2966
acaagagaaa  acggaagaga  gaggaaatga  ggtggggttg  gaggaaaccc  atggggacag   3026
attcccattc  ttagcctaac  gttcgtcatt  gcctcgtcac  atcaatgcaa  aaggtcctga   3086
ttttgttcca  gcaaaacaca  gtgcaatgtt  ctcagagtga  ctttcgaaat  aaattgggcc   3146
caagagcttt  aactcggtct  taaaatatgc  ccaaatttt   actttgtttt  tctttaata   3206 ggctgggcca  catgttggaa  ataagctagt  aatgttgttt  tctgtcaata  ttgaatgtga   3266
tggtacagta  aaccaaaacc  caacaatgtg  gccagaaaga  aagagcaata  ataattaatt   3326
cacacaccat  atggattcta  tttataaatc  acccacaaac  ttgttcttta  atttcatccc   3386
aatcactttt  tcagaggcct  gttatcatag  aagtcatttt  agactctcaa  ttttaaatta   3446
attttgaatc  actaatattt  tcacagttta  ttaatatatt  taatttctat  ttaaatttta   3506 gattatttt   attaccatgt  actgaatttt  tacatcctga  tacccttcc   ttctccatgt   3566 cagtatcatg  ttctctaatt  atcttgccaa  attttgaaac  tacacacaaa  aagcatactt   3626
gcattattta  taataaaatt  gcattcagtg  gcttttaaa   aaaaatgttt  gattcaaaac   3686
tttaacatac  tgataagtaa  gaaacaatta  taatttcttt  acatactcaa  aaccaagata   3746
gaaaaaggtg  ctatcgttca  acttcaaaac  atgtttccta  gtattaagga  ctttaatata   3806
gcaacagaca  aaattattgt  taacatggat  gttacagctc  aaaagattta  taaaagattt   3866
taacctattt  tctcccttat  tatccactgc  taatgtggat  gtatgttcaa  acaccttta   3926 gtattgatag  cttacatatg  gccaaaggaa  tacagtttat  agcaaaacat  gggtatgctg   3986
tagctaactt  tataaaagtg  taatataaca  atgtaaaaaa  ttatatatct  gggaggattt   4046
tttggttgcc  taaagtggct  atagttactg  atttttttatt atgtaagcaa  aaccaataaa   4106
aatttaagtt  tttttaacaa  ctaccttatt  tttcactgta  cagacactaa  ttcattaaat   4166
actaattgat  tgtttaaaag  aaatataaat  gtgacaagtg  gacattattt  atgttaaata   4226
tacaattatc  aagcaagtat  gaagttattc  aattaaaatg  ccacatttct  ggtctctggg   4286
aaaaaaaaaa  aaaaa                                                       4301
```